(12) United States Patent
Fujieda et al.

(10) Patent No.: US 11,160,967 B2
(45) Date of Patent: Nov. 2, 2021

(54) MEDICAL CONNECTOR AND CONNECTING METHOD OF MEDICAL CONNECTOR

(71) Applicant: TERUMO KABUSHIKI KAISHA, Tokyo (JP)

(72) Inventors: Ryouhei Fujieda, Taguig (PH); Yasuhiro Ueda, Kofu (JP); Takeshi Toyama, Minami-Alps (JP)

(73) Assignee: TERUMO KABUSHTKT KAISHA, Tokyo (JP)

( * ) Notice: Subject to any disclaimer, the term of this patent is extended or adjusted under 35 U.S.C. 154(b) by 328 days.

(21) Appl. No.: 16/225,225

(22) Filed: Dec. 19, 2018

(65) Prior Publication Data

US 2019/0117951 A1  Apr. 25, 2019

Related U.S. Application Data

(63) Continuation of application No. PCT/JP2017/022745, filed on Jun. 20, 2017.

(30) Foreign Application Priority Data

Jun. 20, 2016 (JP) .............................. JP2016-121516

(51) Int. Cl.
*A61M 39/10* (2006.01)
*A61M 39/20* (2006.01)

(52) U.S. Cl.
CPC ........ *A61M 39/1011* (2013.01); *A61M 39/20* (2013.01); *A61M 2039/1027* (2013.01); *A61M 2039/1088* (2013.01)

(58) Field of Classification Search
CPC .............. A61M 39/10; A61M 39/1011; A61M 39/105; A61M 39/1055; A61M 39/22; A61M 39/26; A61M 2039/1027; A61M 2039/1016; A61M 2039/1033; A61M 2039/1038; A61M 2039/1044; A61M 2039/1061; A61M 2039/1066;
(Continued)

(56) References Cited

U.S. PATENT DOCUMENTS

| 4,405,163 A | 9/1983 | Voges et al. |
| 4,895,570 A | 1/1990 | Larkin |
| 5,437,650 A | 8/1995 | Larkin et al. |

FOREIGN PATENT DOCUMENTS

| JP | S56-97694 A | 8/1981 |
| JP | H04-227275 A | 8/1992 |

OTHER PUBLICATIONS

International Search Report with English language translation and Written Opinion issued in International Application No. PCT/JP2017/022745 dated Sep. 12, 2017.

*Primary Examiner* — Emily L Schmidt
*Assistant Examiner* — Leah J Swanson
(74) *Attorney, Agent, or Firm* — Foley & Lardner LLP

(57) ABSTRACT

A medical connector includes a tubular male connector unit, an engaging unit arranged on an outer side of the male connector unit in a radial direction of the male connector unit, at least a part of the engaging unit being elastically deformable inward in the radial direction, a locking unit movable between a first position and a second position in which at least a part of the engaging unit is elastically deformed inward in the radial direction relative to the first position, and a blocking mechanism configured to block the locking unit from moving from the first position to the second position in a predetermined state.

14 Claims, 16 Drawing Sheets

(58) Field of Classification Search
CPC .. A61M 2039/1072; A61M 2039/1077; A61M 2039/1083; A61M 2039/1088; A61M 2039/1094; A61M 2039/1022; A61M 2039/267; A61M 25/0014; A61M 39/20; A61M 2039/205
See application file for complete search history.

MEDICAL CONNECTOR AND CONNECTING METHOD OF MEDICAL CONNECTOR

CROSS-REFERENCE TO RELATED APPLICATIONS

The present application is a bypass continuation of PCT Application No. PCT/JP2017/022745, filed on Jun. 20, 2017, which claims priority to Japanese Appl. No. 2016-121516, filed on Jun. 20, 2016. These applications are hereby incorporated by reference in their entireties.

SUMMARY

The present disclosure relates to a medical connector and a connecting method using a medical connector.

Conventionally, a medical connector is used to form a flow path in an infusion set for injecting liquid such as drug solution in a living body such as a patient, other medical devices and the like. Such medical connector is usually connected to a different medical connector. Specifically, a male connector unit provided on one medical connector is inserted in a female connector unit provided on the different medical connector to be connected.

It is also common to provide an engaging unit between the medical connectors in order to prevent occurrence of unintended separation of the medical connectors in a connected state. For example, in the medical connector of a lure lock type, a screw is used as the engaging unit, and the male connector unit is inserted in the female connector unit and screwed, so that they may be connected to each other.

Furthermore, U.S. Pat. No. 4,895,570 discloses a medical connector using a plurality of clips as an engaging unit. The medical connector disclosed in U.S. Pat. No. 4,895,570 includes a pin as a male connector unit, a plurality of internal shoulders as a plurality of clips, and a locking ring as a locking unit. By moving the locking unit to a locked position after inserting a male connector unit in a female connector unit of a different medical connector, a plurality of clips is pressed inward by the locking unit, and are caught by a flange of the female connector unit. As a result, the male connector unit may be put into the locked state in which the male connector is not separated from the female connector unit.

SUMMARY

In the medical connector disclosed in U.S. Pat. No. 4,895,570, before inserting the pin as the male connector unit in the female connector unit of the different medical connector, there is a case in which the locking ring as the locking unit unintentionally moves from an unlocked position to the locked position by some impact, improper operation and the like. In such a case, it is not possible to connect the medical connectors to each other, and operation of moving the locking unit from the locked position to the unlocked position is required before connecting the medical connectors to each other.

Therefore, one object of certain embodiments described in the present disclosure is to provide a medical connector capable of suppressing unintended movement of the locking unit from the unlocked position to the locked position, and a connecting method using a medical connector.

According to one embodiment, a medical connector includes: a tubular male connector unit, an engaging unit arranged on an outer side of the male connector unit in a radial direction of the male connector unit at least a part of which is elastically deformable inward in the radial direction, a locking unit movable between a first position and a second position in which at least a part of the engaging unit is elastically deformed inward in the radial direction relative to the first position, and a blocking mechanism which blocks the locking unit from moving from the first position to the second position in a predetermined state.

In one aspect, the blocking mechanism may be changed between a blocked state in which the locking unit is blocked from moving from the first position to the second position and a movable state in which the locking unit is movable from the first position to the second position.

In one aspect, the engaging unit includes a clip engageable with a female connector unit of a different medical connector by moving inward in the radial direction and a stopper unit formed on a wall surface on an outer side in the radial direction which the locking unit abuts in the blocked state, and the blocking mechanism includes a spacer unit which is interposed between the male connector unit and the clip in the blocked state and which may hold a distance between the male connector unit and the clip to be a predetermined distance or longer, and the stopper unit of the engaging unit.

In one aspect, the blocking mechanism may switch from the blocked state to the movable state by moving or deforming the spacer unit to a position in which a distance between the male connector unit and the clip is allowed to be shorter than the predetermined distance, and the locking unit slides with the stopper unit in the movable state and presses the engaging unit inward in the radial direction, thereby moving the clip inward in the radial direction, and moves from the first position to the second position.

In one aspect, the spacer unit is pressed by the female connector unit to move or deform when the male connector unit is inserted in the female connector unit of the different medical connector and the blocking mechanism is switched from the blocked state to the movable state.

In one aspect, the locking unit moves from the first position to the second position in conjunction with operation of switching from the blocked state to the movable state of the blocking mechanism when the male connector unit is inserted in the female connector unit.

In one aspect, the spacer unit is formed on an annular member provided between the male connector unit and the engaging unit.

In one aspect, the blocking mechanism is capable of switching between the blocked state and the movable state by moving the annular member in an axial direction of the male connector unit.

In one aspect, the annular member includes a deformable portion deformable in an axial direction of the male connector unit and a following portion movable in the axial direction following the deformation of the deformable portion, and the blocking mechanism may be switched between the blocked state in which the following portion is located between the male connector unit and the clip and the movable state in which the following portion is not located between the male connector unit and the clip due to deformation of the deformable portion.

In one aspect, the annular member includes a deformable portion deformable in an axial direction of the male connector unit and a following portion deformable in the axial direction following the deformation of the deformable portion, and the blocking mechanism may be switched between the blocked state in which the following portion is located between the male connector unit and the clip in a state with a predetermined thickness or larger in the radial direction and the movable state in which the following portion is located between the male connector unit and the clip in a state with less than the predetermined thickness in the radial direction by the deformation of the deformable portion.

In one aspect, the following portion includes a distal end face having a diameter reducing portion a diameter of which gradually decreases toward a distal side of the male connector unit on the distal side of the male connector unit, and the diameter reducing portion is brought into contact with the female connector unit in an entire area in a circumferential direction of the male connector unit when the male connector unit is inserted in the female connector unit.

In one aspect, the spacer unit is formed on a cap member detachably mounted so as to cover a distal end of the male connector unit.

According to another embodiment, a connecting method of connecting a medical connector to a different medical connector includes: preparing the medical connector provided with a tubular male connector unit, an engaging unit arranged on an outer side of the male connector unit in a radial direction of the male connector unit at least a part of which is elastically deformable inward in the radial direction, a locking unit movable between a first position and a second position in which at least a part of the engaging unit is elastically deformed inward in the radial direction relative to the first position, and a spacer unit provided between the male connector unit and the engaging unit and a different medical connector provided with a female connector unit in which the male connector unit may be inserted, inserting the male connector unit of the medical connector in the female connector unit of the different medical connector, changing from a blocked state in which the locking unit is blocked from moving from the first position to the second position to a movable state in which the locking unit is allowed to move from the first position to the second position by movement or deformation of the spacer unit being pressed by the female connector unit, and engaging the engaging unit with the female connector unit by elastic deformation inward in the radial direction because the locking unit moves from the first position to the second position and presses the engaging unit inward in the radial direction.

Advantageous Effects of Invention

According to the present disclosure, it is possible to provide a medical connector capable of suppressing unintended movement of the locking unit from the unlocked position to the locked position and a method of connecting a medical connector.

DETAILED DESCRIPTION

Figure 1:
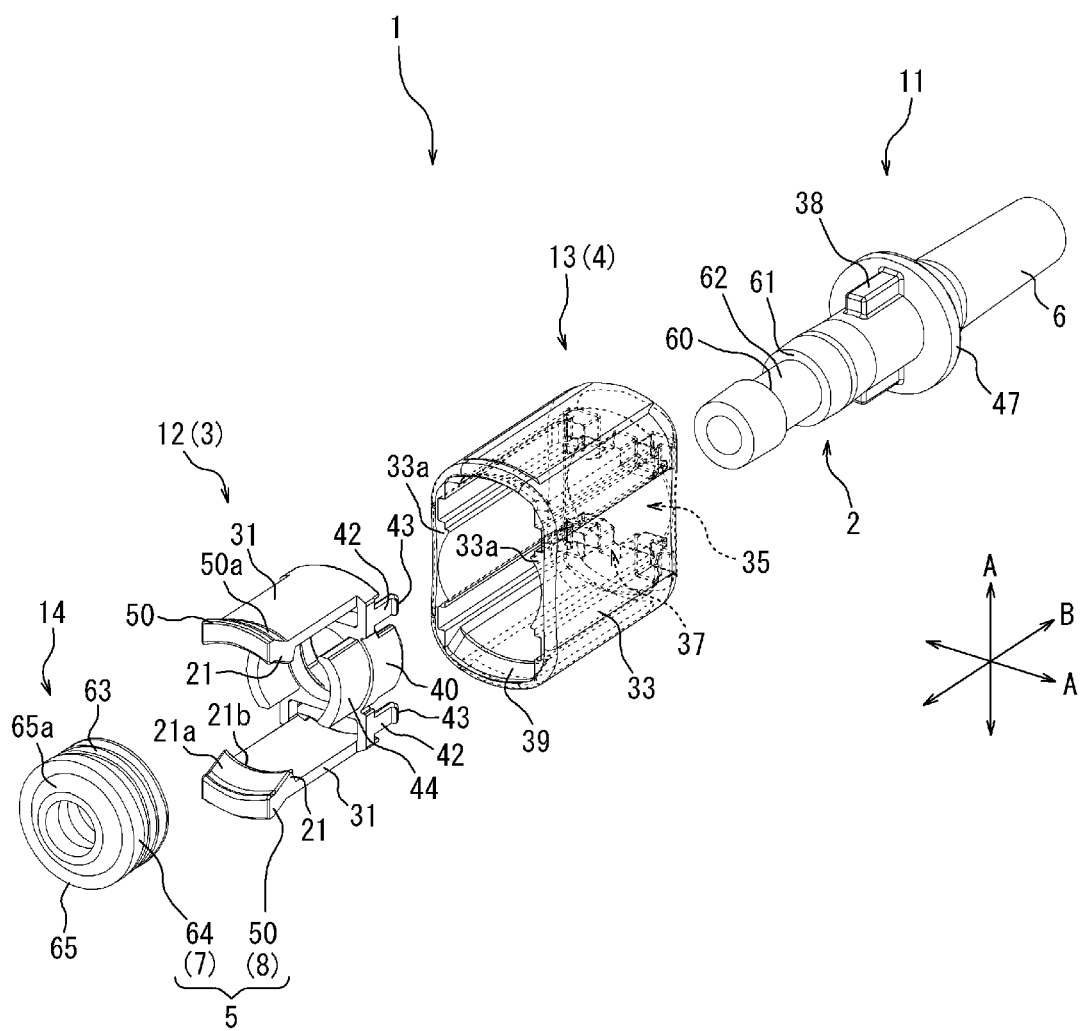
FIG. 1 is an exploded perspective view of a medical connector.

Embodiments of a medical connector and a connecting method of a medical connector according to the present disclosure are described below with reference to FIGS. 1 to 16. Common members and parts in the drawings are assigned the same reference sign. In this specification, a distal side means a distal side of a male connector unit in a direction along a center axis of the male connector unit of the medical connector (for example, a left side in FIG. 3), and a proximal side means the opposite side.

First Embodiment

Figure 2:
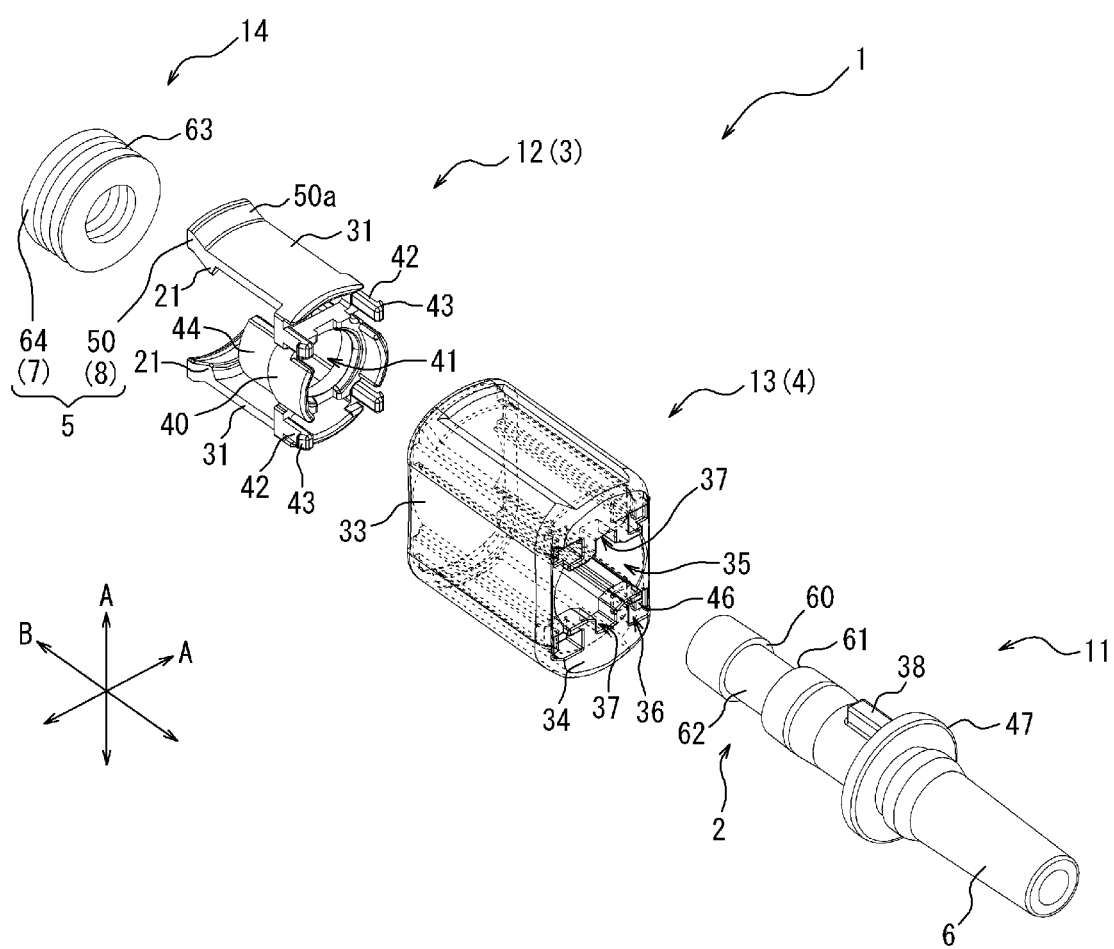
FIG. 2 is an exploded perspective view of a medical connector illustrated in FIG. 1 as seen from an angle different from that of FIG. 1.
Figures 3A, 3B:
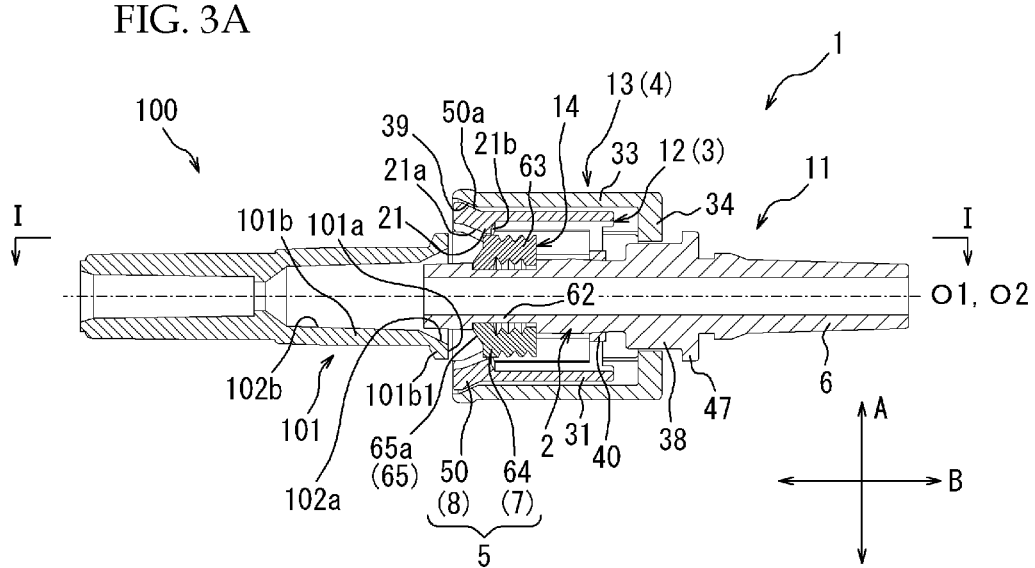
FIG. 3A is a longitudinal sectional view illustrating a separated state of the medical connector illustrated in FIG. 1 and a different medical connector connectable to the medical connector.
FIG. 3B is a cross-sectional view in the same separated state as in FIG. 3A.
Figure 4A:
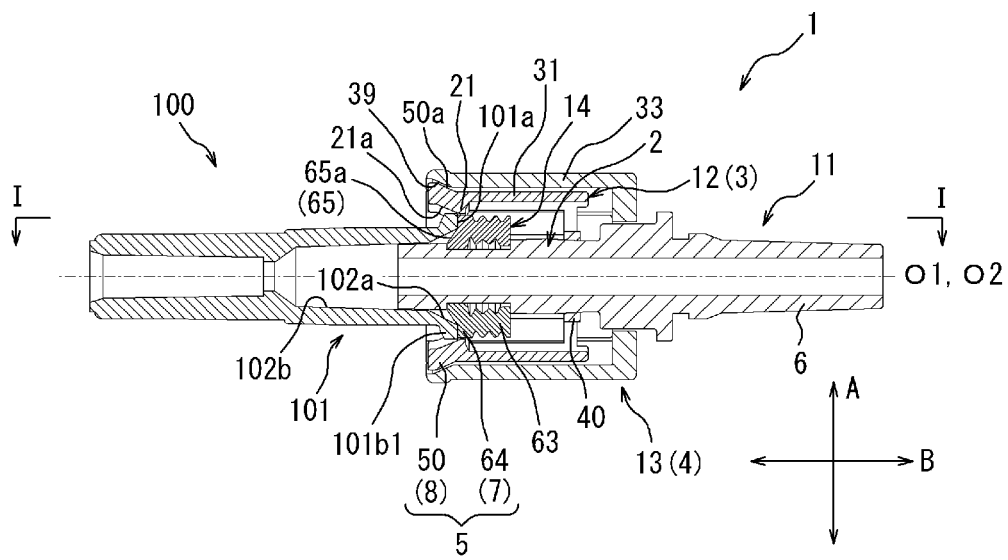
FIG. 4A is a longitudinal sectional view illustrating the medical connector illustrated in FIG. 3 and the different medical connector halfway connected.
Figure 4B:
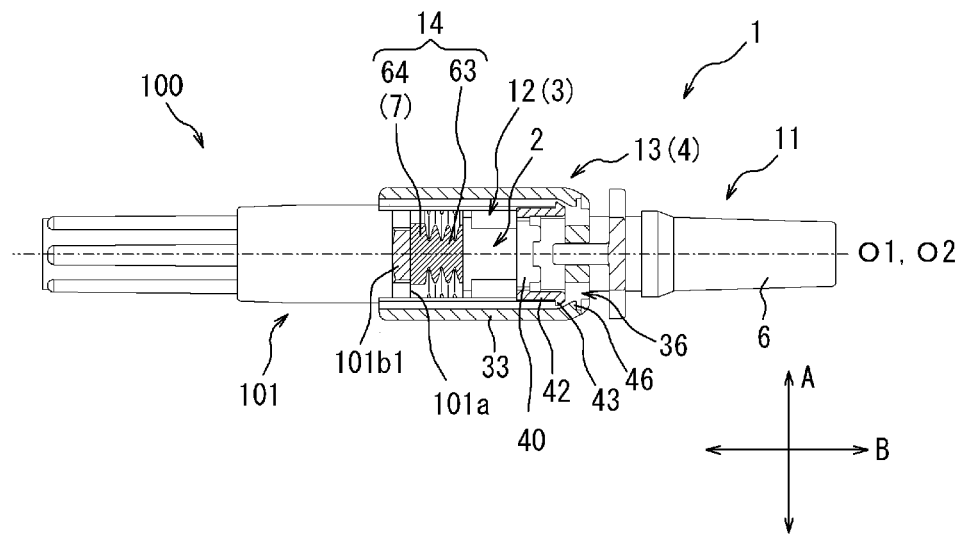
FIG. 4B is a cross-sectional view in the same halfway connected state in FIG. 4A.
Figure 5A:
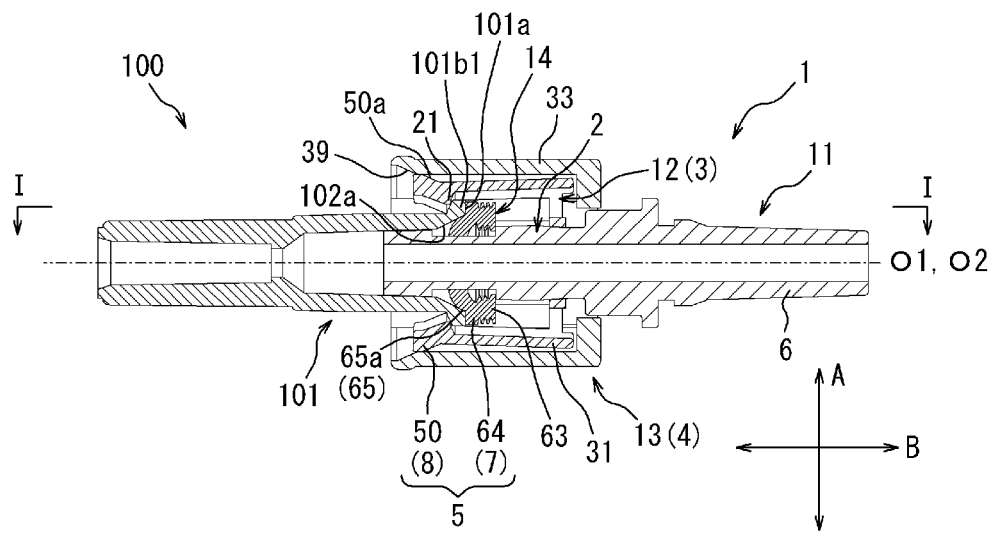
FIG. 5A is a longitudinal sectional view illustrating a state in which the medical connector illustrated in FIG. 3 is completely connected to the different medical connector.
Figure 5B:
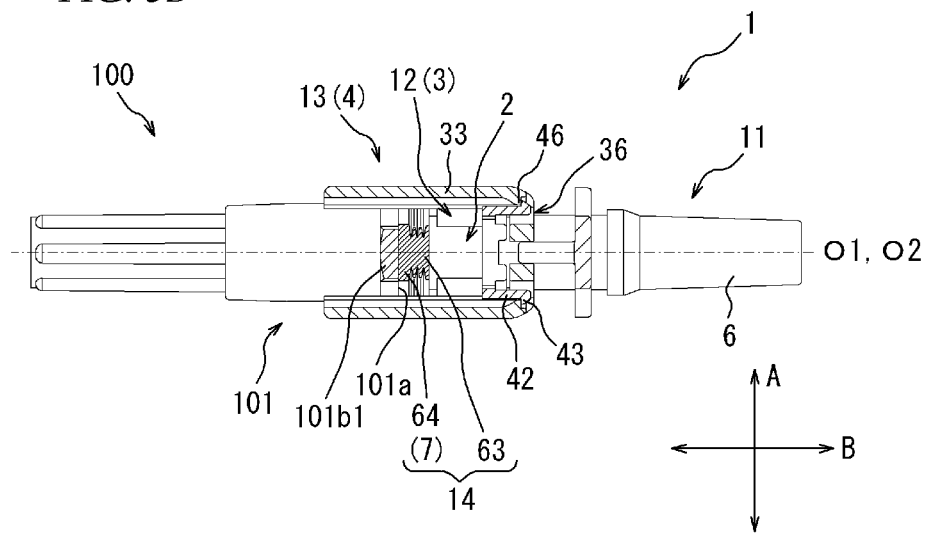
FIG. 5B is a cross-sectional view in the same completely connected state as in FIG. 5A.

FIG. 1 is an exploded perspective view of a medical connector 1 of this embodiment, and FIG. 2 is an exploded perspective view as seen from an angle different from that of FIG. 1. FIG. 3A is a longitudinal sectional view illustrating a separated state before connection of the medical connector 1 to a different medical connector 100 connectable to the medical connector 1, and FIG. 3B is a cross-sectional view in the same separated state as in FIG. 3A. FIG. 4A is a longitudinal sectional view illustrating the medical connector 1 and the different medical connector 100 halfway connected, and FIG. 4B is a cross-sectional view in the same halfway connected state in FIG. 4A. FIG. 5A is a longitudinal sectional view illustrating a state in which the medical connector 1 completely connected to the different medical connector 100, and FIG. 5B is a cross-sectional view in the same completely connected state as in FIG. 5A. FIGS. 3A, 4A, and 5A are longitudinal sectional views including a center axis O1 of a male connector unit 2 of the medical connector 1. FIGS. 3B, 4B, and 5B are cross-sectional views taken along line I-I in FIGS. 3A, 4A, and 5A, respectively.

As illustrated in FIGS. 1 and 2, the medical connector 1 includes the male connector unit 2, an engaging unit 3, a locking unit 4, and a blocking mechanism 5.

The male connector unit 2 is tubular and may be inserted in a female connector unit 101 of the different medical connector 100 as illustrated in FIGS. 3 to 5. Also, as illustrated in FIGS. 1 to 5, the male connector unit 2 of this embodiment is formed integrally with a housing 11.

As illustrated in FIGS. 3 to 5, the engaging unit 3 is arranged on an outer side of the male connector unit 2 in a radial direction A of the tubular male connector unit 2, and at least a part thereof is elastically deformable inward in the radial direction A of the male connector unit 2. More specifically, as illustrated in FIGS. 1 to 5, the engaging unit 3 of this embodiment includes a plurality of clips 21 which may be engaged with the female connector unit 101 of the different medical connector 100 in which the male connector unit 2 is inserted by moving inward in the radial direction A of the male connector unit 2. In other words, a plurality of clips 21 moves to engage with the female connector unit 101 by elastic deformation of at least a part of the engaging unit 3 inward in the radial direction A of the male connector unit 2 in a state in which the male connector unit 2 is inserted in the female connector unit 101 of the different medical connector 100. As illustrated in FIGS. 1 to 5, the engaging unit 3 of this embodiment is formed of an engaging member 12 fixed to the housing 11.

The locking unit 4 may move between a first position and a second position in which at least a part of the engaging unit 3 is elastically deformed inward in the radial direction A of the male connector unit 2 relative to the first position. Specifically, as illustrated in FIG. 3 and the like, the locking unit 4 of this embodiment is arranged on an outer side of the engaging unit 3 in the radial direction A of the male connector unit 2, and is movable in a direction parallel to the center axis O1 of the male connector unit 2 (hereinafter referred to as "axial direction B") with respect to the male connector unit 2 and the engaging unit 3. The locking unit 4 of this embodiment may move in the axial direction B while sliding with respect to the engaging unit 3 and change an elastic deformation amount of the engaging unit 3 according to a position in the axial direction B. As a result, the locking unit 4 may realize the above-described first position and second position.

As an example of a combination of the first position and the second position to which the locking unit 4 may move, there may be an unlocked position and a locked position.

The unlocked position of the locking unit 4 is intended to mean a position of the locking unit 4 in which the clip 21 of the engaging unit 3 may be retreated to a position separated from the female connector unit 101 by a predetermined distance or longer in the radial direction A such that the male connector unit 2 may be inserted in the female connector unit 101 to a predetermined depth and the male connector unit 2 may be removed from the female connector unit 101 in a state in which the male connector unit 2 is inserted to a predetermined depth. The unlocked position of the locking unit 4 in this embodiment is a position illustrated in FIG. 3.

The locked position of the locking unit 4 is intended to mean a position in which the clip 21 of the engaging unit 3 is engaged with the female connector unit 101 such that the male connector unit 2 is not removed from the female connector unit 101 in the state in which the male connector unit 2 is inserted to a predetermined depth. The locked position of the locking unit 4 in this embodiment is a position illustrated in FIG. 5.

As illustrated in FIGS. 1 to 5, the locking unit 4 of this embodiment is formed of a locking member 13 attached to the housing 11 so as to be movable in the axial direction B.

The blocking mechanism 5 blocks the locking unit 4 from moving from the first position to the second position in a predetermined state. Specifically, the blocking mechanism 5 of this embodiment is changeable between a blocked state in which the locking unit 4 is blocked from moving from the first position to the second position and a movable state in which the locking unit 4 is movable from the first position to the second position. In other words, the blocking mechanism 5 of this embodiment may switch whether the locking unit 4 is capable to move between the first position and the second position or not.

More specifically, the blocking mechanism 5 of this embodiment includes a spacer unit 7 and a stopper unit 8. The spacer unit 7 of this embodiment is interposed between the male connector unit 2 and the clip 21 in the blocked state to hold a distance between the male connector unit 2 and the clip 21 to be a predetermined distance or longer in the radial direction A. The stopper unit 8 of this embodiment is a part where the locking unit 4 abuts in the blocked state, and in this embodiment, this is formed on a wall surface on the outer side in the radial direction A of the engaging unit 3.

Furthermore, as illustrated in FIGS. 1 to 5, the spacer unit 7 of the blocking mechanism 5 of this embodiment is formed on an annular member 14 provided between the male connector unit 2 and the engaging unit 3.

The medical connector 1 of this embodiment includes the housing 11 in which the male connector unit 2 is formed, the engaging member 12 fixed to the housing 11 to form the engaging unit 3, the locking member 13 forming the locking unit 4 attached to the housing 11 so as to be slidable in the axial direction B of the male connector unit 2, and the annular member 14 on which the spacer unit 7 of the blocking mechanism 5 is formed; however, the configuration is not limited to this, and a member provided with the male connector unit 2 and the engaging unit 3 may be formed of a single member, for example, by integrally forming the housing 11 and the engaging member 12 of this embodiment as a connector main body. Also, the male connector unit 2, the engaging unit 3, and the locking unit 4 may be formed by combining four or more members.

The housing 11, the engaging member 12, and the locking member 13 may be made of synthetic resin, for example.

Hereinafter, each member and characteristic part of the medical connector 1 of this embodiment are described in detail.

<Housing 11>

As illustrated in FIG. 1 and the like, in the housing 11, a connecting unit 6 to which an end of a medical tube leading to various medical devices such as an infusion container, for example, is connectable is formed on a side opposite to the male connector unit 2. For example, the housing may also be provided with a female connector unit and a mixed injection port unit in addition to the male connector unit. With such housing, it is possible to realize a medical connector referred to as a "T-shaped connector". The housing may also be provided with the female connector unit, the mixed injection port unit, and a flow path switching structure, for example, in addition to the male connector unit. With such housing 11, it is possible to realize a three-way stopcock as the medical connector.

When the mixed injection port unit is provided on the housing, a valve body is provided in an opening of the mixed injection port unit. When a male connector unit of various medical connectors is inserted in the mixed injection port unit, the valve body opens the opening of the mixed injection port unit to allow a flow path in the male connector unit to communicate with a flow path in the housing, and on the other hand, when the male connector unit is not inserted, this closes the opening of the mixed injection port unit.

As illustrated in FIG. 1 and the like, the male connector unit 2 has a substantially cylindrical outer shape, and a flange 47 projecting outward in the radial direction A is provided at a proximal end thereof. On an outer surface of the male connector unit 2, a plurality of (two in this embodiment) ribs 38 extending in the axial direction B is formed in different positions in a circumferential direction of the male connector unit 2. The rib 38 is formed in a position closer to a distal side relative to the flange 47 in the axial direction B.

Furthermore, as illustrated in FIGS. 1 and 2, a small diameter portion 62 of which outer diameter is smaller than that of the distal side and a proximal side in the axial direction B is formed in a position closer to the distal side relative to the rib 38 in the axial direction B on the outer surface of the male connector unit 2 via annular distal side stepped surface 60 and proximal side stepped surface 61. As is described later, the small diameter portion 62 serves as a supporting unit for supporting the annular member 14. That is, the annular member 14 is mounted around the small diameter portion 62 (refer to FIG. 3A). The small diameter portion 62 of this embodiment is formed of a portion of which outer diameter is reduced via the distal side stepped surface 60 and the proximal side stepped surface 61; however, for example, a portion interposed between a distal side flange and a proximal side flange projecting outward in the radial direction A of the male connector unit 2 may be made the small diameter portion 62. In such a case, the distal side stepped surface 60 is formed of a surface on the proximal side of the distal side flange. Also, the proximal side stepped surface 61 is formed of a surface on the distal side of the proximal side flange.

<Engaging Member 12>

As illustrated in FIG. 1 and the like, the engaging member 12 forming the engaging unit 3 includes a plurality of (two in this embodiment) plate pieces 31 having an arc-shaped cross-section extending in the axial direction B, and a bottom wall 40 connected to proximal ends of a plurality of plate pieces 31.

As illustrated in FIG. 2, a through hole 41 penetrating in a thickness direction is defined on the bottom wall 40. The male connector unit 2 is inserted in the through hole 41. In other words, the engaging member 12 is held so as not to be removed from the male connector unit 2 in a state in which an inner surface defining the through hole 41 is supported on the outer surface of the male connector unit 2.

Also, four projections 42 projecting to a side opposite to a plurality of plate pieces 31 are formed on the bottom wall 40. The number of projections 42 provided on the bottom wall 40 may be increased or decreased appropriately. An engaging member side clip 43 which generates a click feeling by getting over a locking member side clip 46 provided on a side of the locking member 13 is formed on a distal end of each projection 42. Furthermore, a cylindrical guide piece 44 extending in the same direction as that of a plurality of plate pieces 31 is provided on the bottom wall 40. The guide piece 44 guides sliding movement of a tubular wall 33 of the locking member 13.

The clip 21 of the engaging member 12 is formed on a distal end of each plate piece 31. Specifically, the clip 21 of this embodiment is a projection projecting inward in the radial direction A of the male connector unit 2 from the distal end of each plate piece 31. The distal side of the plate piece 31 is easily elastically deformed in the radial direction A of the male connector unit 2 as compared with the proximal side continuous to the bottom wall 40. Therefore, by elastically deforming the distal side of the plate piece 31 inward in the radial direction A, it is possible to move the clip 21 in the radial direction A. A tapered surface 21a an amount of projection inward in the radial direction A of which decreases from the proximal side toward the distal side in the axial direction B, in other words, a distance from the center axis O1 in the radial direction A gradually increases is formed in a portion on the distal side in the axial direction B of an apex on an inner side in the radial direction A of each clip 21. Also, a tapered surface 21b an amount of projection inward in the radial direction A of which increases from the proximal side toward the distal side in the axial direction B, in other words, a distance from the center axis O1 in the radial direction A gradually decreases is formed in a portion on the proximal side in the axial direction B of the apex on the inner side in the radial direction A of each clip 21.

Furthermore, on a wall surface on an outer side in the radial direction A of the distal end of each plate piece 31 of the engaging member 12 which is the wall surface on the outer side in the radial direction A of the engaging unit 3, the stopper unit 8 which the locking unit 4 abuts in a case in which the blocking mechanism 5 is in the blocked state is formed. More specifically, on the wall surface on the outer side in the radial direction A of the distal end of each plate piece 31 of the engaging member 12, an outer peripheral side projection 50 projecting outward in the radial direction A is formed, and the stopper unit 8 of this embodiment is formed of the outer peripheral side projection 50. A tapered surface 50a an amount of projection outward in the radial direction A of which increases from the proximal side to the distal side in the axial direction B is formed in a portion on the proximal side in the axial direction B of an apex on an outer side in the radial direction A of the outer peripheral side projection 50.

<Locking Member 13>

The locking member 13 forming the locking unit 4 includes the tubular wall 33 and a bottom wall 34 provided continuously from a proximal side end of the tubular wall 33. As illustrated in FIG. 2, a through hole 35 in which the male connector unit 2 of the housing 11 is inserted is formed in a center portion of the bottom wall 34. Four openings 36 are formed on a peripheral portion of the bottom wall 34 in which the four projections 42 provided on the engaging member 12 may be inserted. The number of openings 36 provided on the locking member 13 may be appropriately increased or decreased according to the number of projections 42 provided on the engaging member 12. The locking member side clip 46 over which the engaging member side clip 43 gets to generate the click feeling is formed on each opening 36.

As described above, the male connector unit 2 is inserted in the through hole 35 formed in the center portion of the bottom wall 34, and the locking member 13 is held on the outer surface of the male connector unit 2 so as to be slidable in the axial direction B on the outer surface of the male connector unit 2.

More specifically, the bottom wall 34 of the locking member 13 is located between the flange 47 provided on the proximal end of the male connector unit 2 and the bottom wall 40 of the engaging member 12 held by the male connector unit 2 so as not to be removed in the axial direction B. The bottom wall 34 may slide between the flange 47 and the bottom wall 40 in the axial direction B. That is, the locking member 13 as a whole may also slide in the axial direction B by a movable range in the axial direction B of the bottom wall 34.

On an inner surface defining the through hole 35 of the bottom wall 34, two concave portions 37 are formed. The locking member 13 is mounted on the male connector unit 2 so that the two concave portions 37 fits the two ribs 38 extending in the axial direction B formed on the outer surface of the male connector unit 2. This makes it possible to prevent the locking member 13 from rotating in the circumferential direction of the male connector unit 2 while making the locking member 13 slidable in the axial direction B.

On the distal end in the axial direction B on the inner peripheral surface of the tubular wall 33 of the locking member 13, a plurality of (two, in this embodiment) tapered surfaces 39 of which diameter expands toward the distal side is provided in positions corresponding to the outer peripheral side projections 50 of the engaging member 12.

<Annular Member 14>

The annular member 14 on which the spacer unit 7 is formed is supported by the outer surface of the small diameter portion 62 of the male connector unit 2 as described above.

Specifically, the annular member 14 of this embodiment includes a deformable portion 63 which may be deformed in the axial direction B of the male connector unit 2 and a following portion 64 as the spacer unit 7 which may move in the axial direction B following the deformation of the deformable portion 63. The blocking mechanism 5 of this embodiment may switch between the blocked state in which the following portion 64 is located so as to be interposed between the male connector unit 2 and the clip 21 in the radial direction A and the movable state in which the following portion 64 is not located so as to be interposed between the male connector unit 2 and the clip 21 in the radial direction A by the deformation of the deformable portion 63. The switching between the blocked state and the movable state of the blocking mechanism 5 is described later in detail (refer to FIGS. 3 to 5).

The following portion 64 of this embodiment is a movable portion which moves in the axial direction B; however, the following portion 64 of the annular member 14 may be made deformable in the axial direction B following the deformation of the deformable portion 63. For example, the following portion 64 may deform in the axial direction B following the deformation of the deformable portion 63 to change a thickness in the radial direction A. In such a case, the blocking mechanism 5 may be configured to switch between the blocked state and the movable state by utilizing variation in thickness in the radial direction A of the following portion 64. For example, it is possible to switch between the blocked state in which the following portion 64 is located in a state with a predetermined thickness or larger in the radial direction A between the male connector unit 2 and the clip 21 and the movable state in which the following portion 64 is located in a state with less than a predetermined thickness in the radial direction A between the male connector unit 2 and the clip 21. The thickness of the following portion 64 in the radial direction A may be made smaller, for example, by elongating the following portion 64 in the axial direction B. An example of such annular member having the following portion which deforms in the axial direction B following the deformation of the deformable portion is described later in detail (refer to FIG. 15).

The deformable portion 63 and the following portion 64 of the annular member 14 of this embodiment are integrally molded of an elastic body such as various rubber materials, for example. Examples of the various rubber materials include natural rubber, isoprene rubber, butadiene rubber, styrene-butadiene rubber, nitrile rubber, chloroprene rubber, butyl rubber, acrylic rubber, ethylene-propylene rubber, hydrin rubber, urethane rubber, silicone rubber, fluorine rubber and the like, for example.

The deformable portion 63 of this embodiment is a bellows tubular portion formed of a bellows-shaped peripheral wall, and is elastically deformable in the axial direction B. The following portion 64 of this embodiment is continuous to one end on the distal side in the axial direction B of the bellows tubular portion as the deformable portion 63, and a central opening communicated with a hollow portion of the deformable portion 63 is formed in a center portion thereof.

The male connector unit 2 is inserted so as to penetrate the hollow portion of the deformable portion 63 and the central opening of the following portion 64, and the annular member 14 is arranged on the outer surface of the small diameter portion 62 as described above. An inner surface defining the central opening of the following portion 64 is brought into close contact so as to press the outer surface of the small diameter portion 62 in a state in which the annular member 14 is arranged on the outer surface of the small diameter portion 62. In other words, a diameter of the central opening is smaller than an outer diameter of the small diameter portion 62, and in a state in which the small diameter portion 62 is inserted in the central opening, the inner surface defining the central opening is brought into close contact with the outer surface of the small diameter portion 62 by elastic force.

The annular member 14 is interposed between the distal side stepped surface 60 and the proximal side stepped surface 61 on the outer surface of the small diameter portion 62. That is, one end on the distal side in the axial direction B of the annular member 14 abuts the distal side stepped surface 60, and one end on the proximal side in the axial direction B of the annular member 14 abuts the proximal side stepped surface 61. More specifically, the annular member 14 is such that one end on the proximal side of the deformable portion 63 abuts the proximal side stepped surface 61 and one end on the distal side of the following portion 64 abuts the distal side stepped surface 60, so that the position in the axial direction B on the outer surface of the male connector unit 2 is determined. The deformable portion 63 of this embodiment is in a state of being compressed and deformed in a state in which the annular member 14 abuts the distal side stepped surface 60 and the proximal side stepped surface 61 to be interposed therebetween, but the configuration is not limited to this, and, for example, it may also be configured such that the deformable portion 63 is in a natural state in the state in which the annular member 14 abuts the distal side stepped surface 60 and the proximal side stepped surface 61.

The following portion 64 of this embodiment is molded of an elastic body integrally with the deformable portion 63, but this may also be, for example, the following portion 64 molded of an elastic body different from that of the deformable portion 63. Also, the following portion 64 may also be molded of a hard material harder than that of the deformable portion 63 such as a resin material, for example.

Especially, in a case of moving in the axial direction B following the deformation in the axial direction B of the deformable portion 63 as the following portion 64 in this embodiment, it is preferable that the following portion 64 is less likely to be deformed in the axial direction B as compared with the deformable portion 63 and the deformable portion 63 is preferentially deformed in the axial direction B. In such a case, it is especially preferable that the following portion 64 is molded separately from the deformable portion 63 of an elastic body, a synthetic resin or the like harder than that of the deformable portion 63. For example, an elastic body or a synthetic resin harder than that of the deformable portion 63 may be realized by forming the following portion 64 using a material having a higher elastic modulus than that of the deformable portion 63, for example.

On the other hand, in a case in which the following portion 64 is elongated to be deformed in the axial direction B so as to be thinner in the radial direction A following the deformation of the deformable portion 63 in the axial direction B, the following portion 64 is preferably configured to be easily deformed in the axial direction B as the deformable portion 63. In such a case, it is especially preferable that the following portion 64 is molded integrally with or separately from the deformable portion 63 of an elastic body as hard as that of the deformable portion 63 or molded separately from the deformable portion 63 of an elastic body softer than that of the deformable portion 63. An example of such annular member having the following portion which deforms in the axial direction B following the deformation of the deformable portion is described later in detail (refer to FIG. 15). For example, the elastic body softer than that of the deformable portion 63 may be realized by forming the following portion 64 using a material whose elastic modulus is smaller than that of the deformable portion 63.

The following portion 64 of this embodiment has a diameter reducing portion 65a of which diameter gradually decreases from the proximal side toward the distal side in the axial direction B of the male connector unit 2 on a distal end face 65 on the distal side in the axial direction B. Due to the diameter reducing portion 65a, the diameter of the central opening of the following portion 64 is smaller than an inner diameter of the bellows tubular portion as the deformable portion 63.

Out of the following portion 64 of this embodiment, an outer surface on an outer side in the radial direction A which the clip 21 abuts does not have a bellows shape and is formed of a smooth peripheral surface; however, the outer surface shape is not limited to this and may be appropriately changed according to a shape of the clip 21, a position of the clip 21 and the like.

<Blocking Mechanism 5 Formed of Spacer Unit 7 and Stopper Unit 8>

The blocking mechanism 5 of this embodiment is formed of the spacer unit 7 formed on the above-described annular member 14 and the stopper unit 8 formed on the above-described engaging member 12. The blocking mechanism 5 of this embodiment may switch between a state in which the elastic deformation of the engaging unit 3 inward in the radial direction A, more specifically, elastic deformation of the plate piece 31 of the engaging member 12 inward in the radial direction A is blocked and this is allowed by the movement of the following portion 64 as the spacer unit 7. In a state in which the spacer unit 7 blocks the elastic deformation of the engaging unit 3 inward in the radial direction A, the locking unit 4 is blocked by the stopper unit 8, so that this cannot move from the first position to the second position. On the other hand, in a state in which the spacer unit 7 allows the elastic deformation of the engaging unit 3 inward in the radial direction A, the locking unit 4 is not blocked by the stopper unit 8 and may move from the first position to the second position. In this manner, the blocking mechanism 5 of this embodiment may change between the blocked state in which the locking member 13 forming the locking unit 4 is blocked from moving from the first position to the second position and the movable state in which the locking member 13 forming the locking unit 4 is movable from the first position to the second position.

Figure 16:
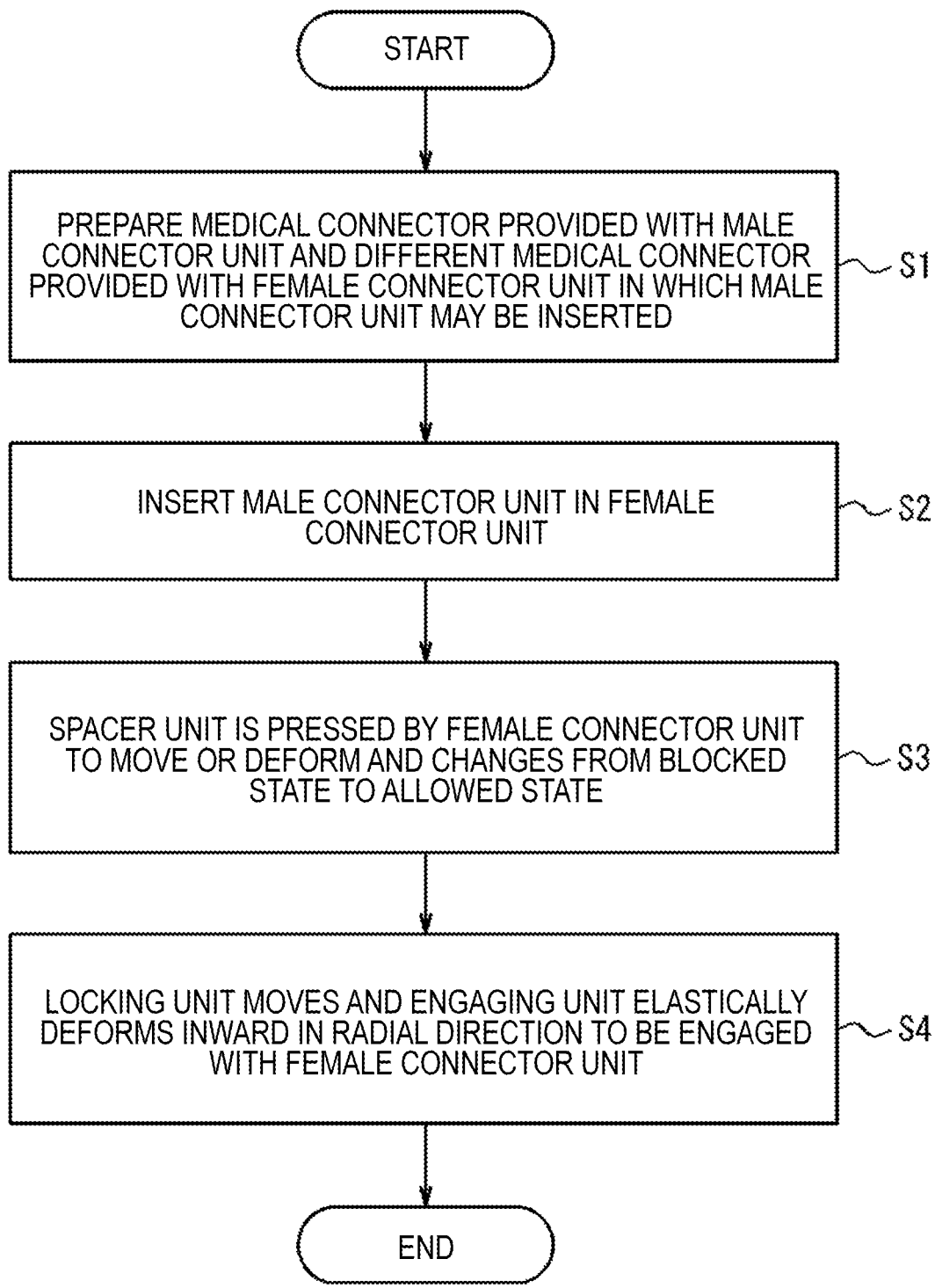
FIG. 16 is a flowchart illustrating a connecting method of a medical connector.

Next, with reference to FIGS. 3 to 5 and FIG. 16, a manner of connecting the above-described medical connector 1 to the different medical connector 100 is described. FIG. 16 is a flowchart illustrating a connecting method of connecting the medical connector 1 to the different medical connector 100.

First, a configuration of the different medical connector 100 is described. The different medical connector 100 illustrated in FIGS. 3 to 5 includes the female connector unit 101 as described above, and in this embodiment, this is configured as an indwelling needle hub connected to an indwelling needle (not illustrated). An inner peripheral surface of the female connector unit 101 is formed in a tapered shape of which diameter gradually decreases inward on a center axis O2 (which coincides with the center axis O1 in FIGS. 3 to 5) of the female connector unit 101. More specifically, the inner peripheral surface of the female connector unit 101 includes a first tapered portion 102a located in the vicinity of a top surface 101a of which diameter gradually decreases inward on the center axis O2, and a second tapered portion 102b continuous inward the first tapered portion 102a with inclination with respect to the center axis O2 smaller than that of the first tapered portion 102a. An inclination angle of the second tapered portion 102b with respect to the center axis O2 is the same as the inclination angle of the tapered outer peripheral surface of the distal end of the male connector unit 2 with respect to the center axis O1.

The female connector unit 101 is also provided with a cylindrical peripheral wall portion 101b. A plurality of (two in this embodiment) engaging convex portions 101b1 projecting outward in the radial direction is formed in positions in the vicinity of the top surface 101a which is one end face of the peripheral wall portion 101b out of the outer surface of the peripheral wall portion 101b.

A connecting method of connecting the medical connector 1 to the different medical connector 100 will next be described. As illustrated in FIG. 16, the connecting method of the medical connectors herein illustrated includes step S1 of preparing the medical connector 1 and the different medical connector 100 provided with the female connector unit 101 in which the male connector unit 2 may be inserted, step S2 of inserting the male connector unit 2 of the medical connector 1 in the female connector unit 101 of the different medical connector 100, step S3 at which the spacer unit 7 moves or deforms in the axial direction B by being pressed by the female connector unit 101 and it changes from the blocked state in which the locking unit 4 is blocked from moving from the first position to the second position to the movable state in which the locking unit 4 is movable from the first position to the second position, and step S4 in which the locking unit 4 moves from the first position to the second position and presses the engaging unit 3 inward in the radial direction A, so that the engaging unit 3 is elastically deformed inward in the radial direction A to be engaged with the female connector unit 101. Hereinafter, the connecting method of the medical connector is described in detail.

First, the medical connector 1 and the different medical connector 100 are prepared. Then, from the state in which the medical connector 1 and the different medical connector 100 are separated from each other as illustrated in FIG. 3, when the different medical connector 100 is held by a left hand and the locking member 13 of the medical connector 1 is held by a right hand, for example, the locking member 13 is moved in a direction to approach the different medical connector 100, and the male connector unit 2 of the medical connector 1 is inserted in the female connector unit 101 of the different medical connector 100, the top surface 101a of the female connector unit 101 abuts the distal end face 65 of the annular member 14 in the entire area in the circumferential direction of the male connector unit 2 as illustrated in FIG. 4. As a result, it becomes possible to liquid-tightly communicate the flow path in the male connector unit 2 and the flow path in the female connector unit 101.

As described above, the distal end face 65 of the following portion 64 of the annular member 14 of this embodiment includes the diameter reducing portion 65a, and as illustrated in FIG. 5 to be referred to later, the diameter reducing portion 65a is brought into contact with the female connector unit 101 not only on the top surface 101a of the female connector unit 101 but also over the entire area in the circumferential direction of the male connector unit 2 across the first tapered portion 102a on the inner peripheral surface of the female connector unit 101. As a result, it is possible to further improve liquid tightness between the flow path in the male connector unit 2 and the flow path in the female connector unit 101.

From the viewpoint of ensuring the liquid tightness between the flow path in the male connector unit 2 and the flow path in the female connector unit 101, the distal end face 65 is only required to be in contact with at least one of the top surface 101a of the female connector unit 101, the inner peripheral surface of the female connector unit 101, and an inner edge of the top surface 101a of the female connector unit 101 in the entire area in the circumferential direction of the male connector unit 2. However, in consideration of suppressing retention and the like of liquid such as drug solution in the communicated flow path, the distal end face 65 is preferably brought into contact with at least the inner peripheral surface of the female connector unit 101 or the inner edge of the top surface 101a of the female connector unit 101 in the entire area in the circumferential direction of the male connector unit 2. Therefore, in a case of the distal end face 65 including the diameter reducing portion 65a as in this embodiment, the diameter reducing portion 65a is easily brought into contact with at least the inner peripheral surface of the female connector unit 101 or the inner edge of the top surface 101a of the female connector unit 101. As a result, securing of liquid tightness and suppression of retention of liquid may be easily realized at the same time. It is especially preferable in the viewpoint of the liquid tightness and the retention suppression that the diameter reducing portion 65a is configured to be brought into contact with the female connector unit 101 in the entire area in the circumferential direction of the male connector unit 2 not only on the top surface 101a of the female connector unit 101 but also across the first tapered portion 102a on the inner peripheral surface of the female connector unit 101 as in this embodiment.

A minimum rotation diameter of a plurality of clips 21 around the center axis O1 (in this embodiment, a minimum value of an opposing distance between the two clips 21 in the radial direction A, the same as a distance in the radial direction A between apices of the two clips 21) is larger than an outer diameter of a portion in which the engaging convex portions 101b1 are provided of the female connector unit 101 (in this embodiment, distance between opposing portions across the center axis O2 on the outer peripheral side ends of the two engaging convex portions 101b1), so that it is possible to allow a plurality of clips 21 of the engaging member 12 to go beyond the engaging convex portions 101b1 of the female connector unit 101 without getting over the engaging convex portions 101b1 of the female connector unit 101 when the male connector unit 2 is inserted in the female connector unit 101. Therefore, when the medical connector 1 is connected to the different medical connector 100, the clip 21 does not get over the stepped portion and the like of the different medical connector 100 while strongly pressing the same, so that it becomes possible to make it difficult to cause unintended displacement in the different medical connector 100. Furthermore, the tapered surface 21a of a plurality of clips 21 may smoothly guide the engaging convex portion 101b1 of the female connector unit 101 between a plurality of clips 21.

In a state illustrated in FIGS. 3 and 4, the blocking mechanism 5 is in the blocked state. Specifically, the following portion 64 as the spacer unit 7 of the annular member 14 is located between the clip 21 and an outer wall of the male connector unit 2 in the radial direction A, and the clip 21 cannot move inward in the radial direction A. In other words, the distance between the male connector unit 2 and the clip 21 in the radial direction A is prevented from being shorter than a predetermined distance (for example, the thickness in the radial direction A of the following portion 64) with the following portion 64 interposed therebetween. Therefore, the locking member 13 abuts the outer peripheral side projection 50 as the stopper unit 8 of the engaging member 12, so that this cannot slide from the proximal side to the distal side in the axial direction B, that is, from the first position to the second position.

When the locking member 13 is further moved from the state illustrated in FIG. 4 in a direction to approach the different medical connector 100, the annular member 14 is pressed by the top surface 101a of the female connector unit 101, and as a result, the annular member 14 is compressed to be deformed. More specifically, the deformable portion 63 of the annular member 14 is compressed to be deformed in the axial direction B by being pressed by the top surface 101a of the female connector unit 101, and accordingly, the following portion 64 moves from the distal side to the proximal side in the axial direction B. As a result, as illustrated in FIG. 5, the following portion 64 is no longer located between the clip 21 and the outer wall of the male connector unit 2 in the radial direction A. That is, in the state illustrated in FIG. 5, the blocking mechanism 5 changes from the blocked state illustrated in FIG. 4 to the movable state. FIG. 5 illustrates a state in which the locking member 13 completes the movement from the first position to the second position after the blocking mechanism 5 changes from the blocked state to the movable state.

As described above, the blocking mechanism 5 of this embodiment may be switched from the blocked state to the movable state by moving the following portion 64 as the spacer unit 7 to a position in which it is allowed that the distance between the male connector unit 2 and the clip 21 in the radial direction A becomes shorter than a predetermined distance. When the male connector unit 2 is inserted in the female connector unit 101 of the different medical connector 100, the following portion 64 as the spacer unit 7 of this embodiment moves by being pressed by the female connector unit 101, and the blocking mechanism 5 may be switched from the blocked state to the movable state.

When the blocking mechanism 5 is in the movable state, the locking member 13 forming the locking unit 4 may slide with the outer peripheral side projection 50 as the stopper unit 8 of the engaging member 12 forming the engaging unit 3 and may move from the first position to the second position. During this movement, the locking member 13 forming the locking unit 4 presses the plate piece 31 of the engaging member 12 forming the engaging unit 3 inward in the radial direction A, thereby elastically deforming the plate piece 31 with a connecting portion with the bottom wall 40 as a fulcrum and moving the clip 21 inward in the radial direction A. FIG. 5 illustrates a state in which the clip 21 moves inward in the radial direction A and is engaged with the female connector unit 101.

The locking member 13 of this embodiment moves from the first position to the second position while sliding the tapered surface 39 of the tubular wall 33 with the tapered surface 50a of the outer peripheral side projection 50, so that it is possible to reduce operating force for elastically deforming a plurality of plate pieces 31. Either such tapered surface 39 or tapered surface 50a for reducing the operation force may also be omitted.

By moving a plurality of clips 21 inward in the radial direction A by the locking member 13 in this manner, as illustrated in FIG. 5, it enters a locked state in which the plurality of clips 21 cannot be removed from the different medical connector 100. Herein, the "locked state" means a state in which a plurality of clips 21 is pressed by the tubular wall 33 of the locking member 13 forming the locking unit 4 and locked on the engaging convex portion 101b1 of the female connector unit 101 so as not to be removable in this embodiment. More specifically, in this embodiment, this means a state in which the tapered surface 21b of a plurality of clips 21 abuts the engaging convex portion 101b1 of the female connector unit 101 so as to be caught by the same. In this embodiment, the connection between the medical connector 1 to the different medical connector 100 is completed when it enters such locked state.

As described above, it is preferable that the medical connector 1 is connected to the different medical connector 100 in a state of gripping the locking member 13. By connecting in this manner, the locking member 13 forming the locking unit 4 moves from the first position to the second position in conjunction with operation in which the blocking mechanism 5 is switched from the blocked state to the movable state when the male connector unit 2 is inserted in the female connector unit 101. That is, it is possible to realize a configuration in which the switching of the blocking mechanism 5 and the movement of the locking member 13 may be executed in conjunction only by operation in one direction with a simple configuration by making a direction of external force required for switching the blocking mechanism 5 from the blocked state to the movable state (in this embodiment, the same direction as the moving direction of the following portion 64) and a moving direction to move the locking member 13 from the first position to the second position parallel to each other and directions opposite to each other.

Especially, in this embodiment, the direction of the external force required for switching the blocking mechanism 5 from the blocked state to the movable state (the same direction as the movement direction of the following portion 64 in this embodiment) and the moving direction to move the locking member 13 from the first position to the second position are made parallel to the axial direction B. Therefore, it is possible to perform the switching from the blocked state to the movable state of the blocking mechanism 5 and the movement from the first position to the second position of the locking member 13 in conjunction only by operation in one direction to approach both the medical connectors in the axial direction B in order to insert the male connector unit 2 in the female connector unit 101. That is, it is possible to complete the connection between the medical connector 1 and the different medical connector 100 only by operation in one direction of inserting the male connector unit 2 in the female connector unit 101 of the different medical connector 100.

Furthermore, in this embodiment, in order to surely maintain the locked state and the completely connected state described above, mutual rotation around the center axis O1 and the center axis O2 between the female connector unit 101 and the locking member 13 is regulated. Specifically, the tubular wall 33 of the locking member 13 includes a rotation blocking unit 33a (refer to FIG. 1) of blocking the rotation of the female connector unit 101 with respect to the tubular wall 33 in such connected state. In this embodiment, the rotation blocking unit 33a is formed as a convex projecting from the inner peripheral surface of the tubular wall 33, and when the female connector unit 101 rotates with respect to the tubular wall 33, this may abut a plurality of engaging convex portions 101b1 (refer to FIG. 3 and the like) of the female connector unit 101 to block further rotation of the female connector 101, thereby maintaining the locking state between a plurality of engaging convex portions 101b1 and a plurality of clips 21.

As illustrated in FIGS. 3B, 4B, and 5B, when the tubular wall 33 puts a plurality of clips 21 (refer to FIG. 3A and the like) into the locked state, the click feeling is generated by the four locking member side clips 46 getting over the four engaging member side clips 43. With this click feeling, an operator may easily confirm that it is completely locked.

The medical connector 1 may be connected to the different medical connector 100 in the manner as described above; however, when connecting, it is not required that a plurality of clips 21 gets over the engaging convex portion 101b1 of the female connector unit 101. Therefore, according to the medical connector 1, unintended displacement of the different medical connector 100 may be suppressed when connecting to the different medical connector 100. In this embodiment, projections (locking member side clip 46 and engaging member side clip 43) for generating the click feeling are provided; it goes without saying that a size and a shape of the projections are set such that force required to get over the projections when generating the click feeling is sufficiently small force such that the extent that unintended displacement of the different medical connector 100 does not occur.

After connecting the medical connectors to each other in this manner, for example, an adhesive sheet such as a dressing film is attached to the skin of a living body of a patient and the like in which the indwelling needle is placed so as to cover the female connector unit 101 and the locking member 13, so that the movement of the locking member 13 is suppressed, and occurrence of unintended separation of the connector may be suppressed.

When separating the medical connectors from each other, by moving the locking member 13 from the distal side toward the proximal side in the axial direction B with respect to the housing 11 and the engaging member 12, that is, from the second position to the first position, a plurality of plate pieces 31 is restored from the elastic deformation and a plurality of clips 21 is retreated outward in the radial direction A so as to move away from the female connector unit 101. Specifically, a plurality of clips 21 are moved to the state illustrated in FIG. 3A. As a result, the locked state by the locking member 13 may be released. When the locked state is released as described above, the top surface 101a of the female connector unit 101 is pressed from the proximal side toward the distal side in the axial direction B, that is, in a direction in which the medical connectors are separated from each other in the axial direction B by the restoring force of the annular member 14 in which the deformable portion 63 is in a compressed state. As a result, it is possible to easily separate the medical connectors from each other.

Furthermore, when the deformable portion 63 is restored, the following portion 64 of the annular member 14 moves from the proximal side to the distal side in the axial direction B in a state of abutting the top surface 101a and the first tapered portion 102a of the female connector unit 101 halfway removed, and is restored to an initial position before being connected to the female connector unit 101. That is, the following portion 64 of the annular member 14 is restored to a position in which this is interposed between the clip 21 and the outer wall of the male connector unit 2 in the radial direction A so that the clip 21 cannot move inward in the radial direction A, and as a result, the blocking mechanism 5 is put into the blocked state again. More specifically, the annular member 14 of this embodiment is restored until the distal end face 65 abuts the distal side stepped surface 60.

In this manner, according to the annular member 14 of this embodiment provided with the deformable portion 63 and the following portion 64, each time the medical connector 1 and the different medical connector 100 are connected, the blocking mechanism 5 may be switched from the blocked state to the movable state, and each time the different medical connector 100 is removed from the medical connector 1, the blocking mechanism 5 may be switched from the movable state to the blocked state. That is, it is possible to realize the medical connector 1 provided with the blocking mechanism 5 which may be repeatedly used capable of switching between the blocked state and the movable state a plurality of number of times.

In this embodiment, a projecting width of the locking member side clip 46 and the engaging member side clip 43 described above may be enlarged so that the locking cannot be released once the locking by the locking member 13 is completed, thereby preventing unintended separation between the medical connector 1 and the different medical connector 100 from occurring.

As described above, the medical connector 1 of this embodiment includes the blocking mechanism 5 which blocks the locking unit 4 from moving from the first position to the second position in a predetermined state, so that it is possible to suppress unintended movement of the locking unit 4 from the unlocked position to the locked position before connecting the medical connector 1 to the different medical connector 100.

Furthermore, the blocking mechanism 5 of this embodiment may change between the blocked state in which the locking unit 4 is blocked from moving from the first position to the second position and the movable state in which the locking unit 4 is movable from the first position to the second position, so that the medical connector 1 may be easily connected to the different medical connector 100 by putting into the movable state when the medical connector 1 is connected to the different medical connector 100.

Figure 15:
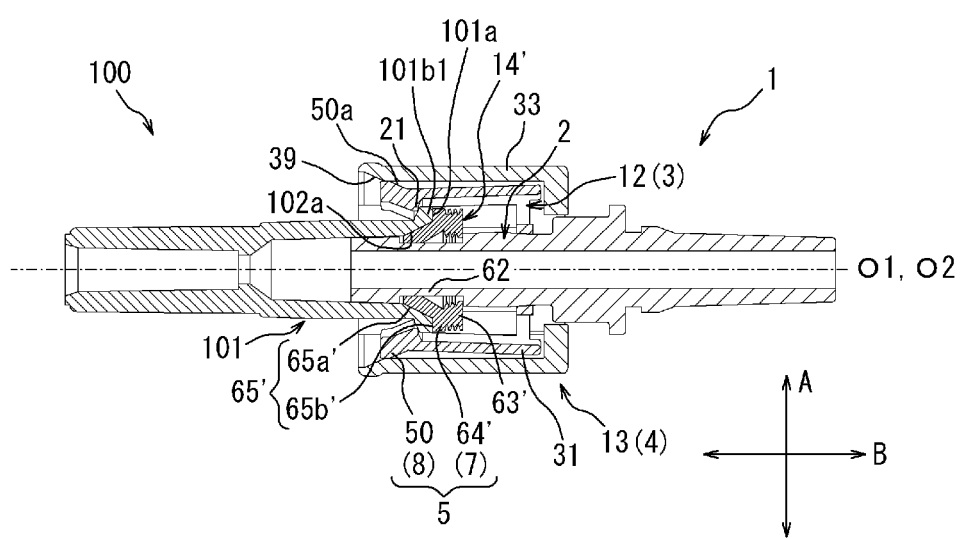
FIG. 15 is a longitudinal sectional view illustrating a state in which connection between the medical connector provided with an annular member as a variation of the annular member illustrated in FIG. 1 and the different medical connector is completed.

The annular member 14 of this embodiment includes the deformable portion 63 which may be deformed in the axial direction B of the male connector unit 2 and the following portion 64 which may move in the axial direction B following the deformation of the deformable portion 63; however, this may be an annular member 14' provided with a deformable portion 63' deformable in the axial direction B of the male connector unit 2 and a following portion 64' deformable in the axial direction B following the deformation of the deformable portion 63' as illustrated in FIG. 15. The annular member 14' illustrated in FIG. 15 has a shape similar to that of the above-described annular member 14 (refer to FIGS. 1 to 5), and is supported on the outer surface of the small diameter portion 62 of the male connector unit 2 as is the case with the above-described annular member 14. The deformable portion 63' of the annular member 14' is pressed by the female connector unit 101 to be compressed and deformed in the axial direction B when the male connector unit 2 is inserted in the female connector unit 101 as is the case with the deformable portion 63 of the annular member 14. However, the following portion 64' of the annular member 14' does not move in the axial direction B following the compression deformation of the deformable portion 63' in the axial direction B, but is elongated to be deformed in the axial direction B following the compression deformation of the deformable portion 63' in the axial direction B. More specifically, a distal end face 65' of the following portion 64' illustrated in FIG. 15 has a diameter reducing portion 65a' of which diameter gradually decreases from the proximal side to the distal side in the axial direction B of the male connector unit 2 in a center portion thereof. The distal end face 65' includes an annular flat portion 65b' extending in a direction orthogonal to the axial direction B around the diameter reducing portion 65a' on an outer side in the radial direction A.

When the male connector unit 2 is inserted in the female connector unit 101, the top surface 101a of the female connector unit 101 abuts the annular flat portion 65b' and presses the annular flat portion 65b' toward the proximal side in the axial direction B. As a result, the position of the annular flat portion 65b' moves toward the proximal side in the axial direction B. On the other hand, a position on the distal side in the axial direction B of the diameter reducing portion 65a' slightly moves in the axial direction B or does not move in the axial direction B by being interposed between the outer surface of the male connector unit 2 and the inner surface of the female connector unit 101 and/or by frictional force between the inner surface defining a central opening of the following portion 64' and the outer surface of the small diameter portion 62 of the male connector unit 2. That is, when inserting the male connector unit 2 in the female connector unit 101, the following portion 64' is elastically deformed in the axial direction B to elongate because the annular flat portion 65b' moves toward the proximal side in the axial direction B with an end on the distal side in the axial direction B of the diameter reducing portion 65a' as an origin (refer to FIG. 15). As a result, it is possible to reduce the thickness of the following portion 64' in the radial direction A. In the example illustrated in FIG. 15, as described above, by using change in the thickness in the radial direction A, the blocked state and the movable state of the blocking mechanism 5 are switched.

FIG. 15 is a view illustrating the annular member 14' in a state in which the connection between the medical connector 1 and the different medical connector 100 is completed; the annular member 14' in a state in which the medical connector 1 and the different medical connector 100 is separated is similar to the annular member 14 illustrated in FIG. 3.

Next, a medical connector 201 as a variation of the above-described medical connector 1 is described with reference to FIGS. 6 to 10.

Figure 6:
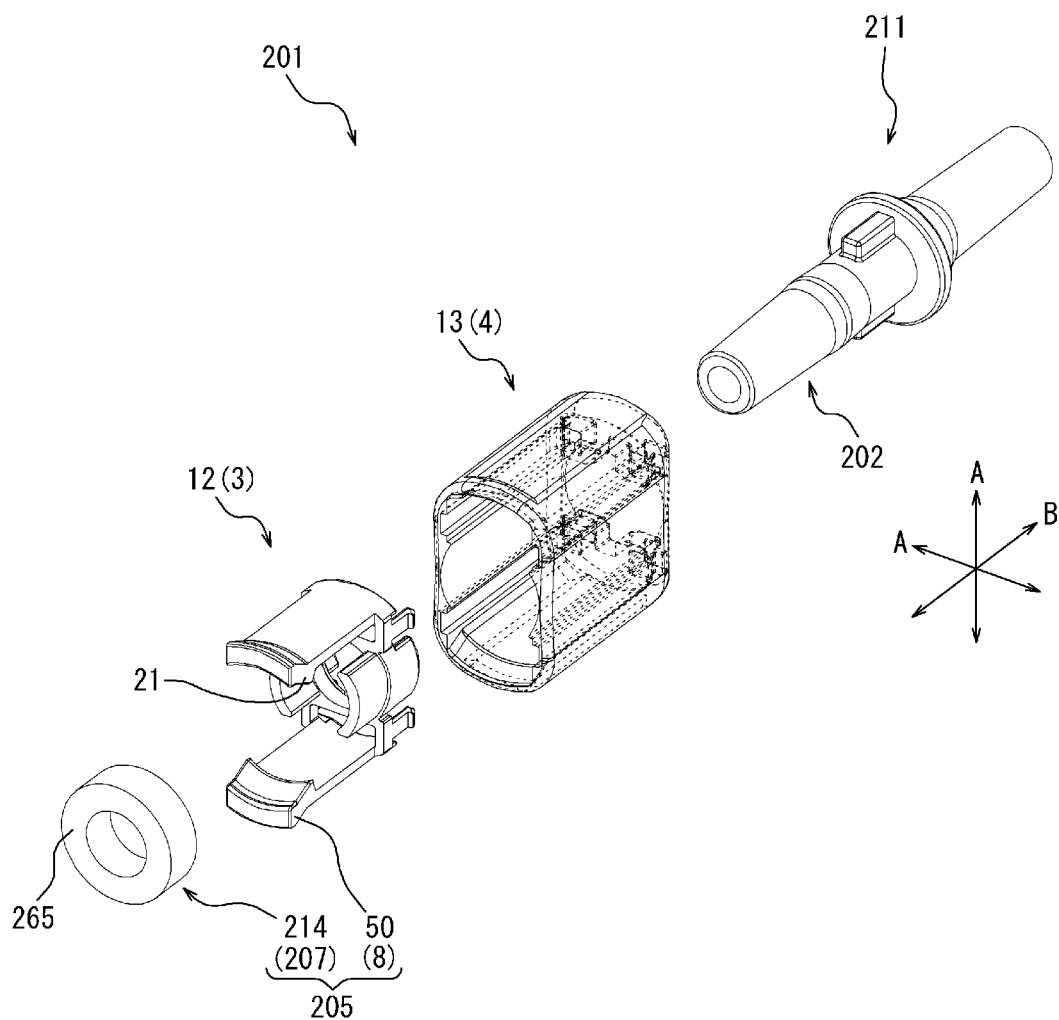
FIG. 6 is an exploded perspective view of a medical connector as a variation of the medical connector illustrated in FIG. 1.
Figure 7:
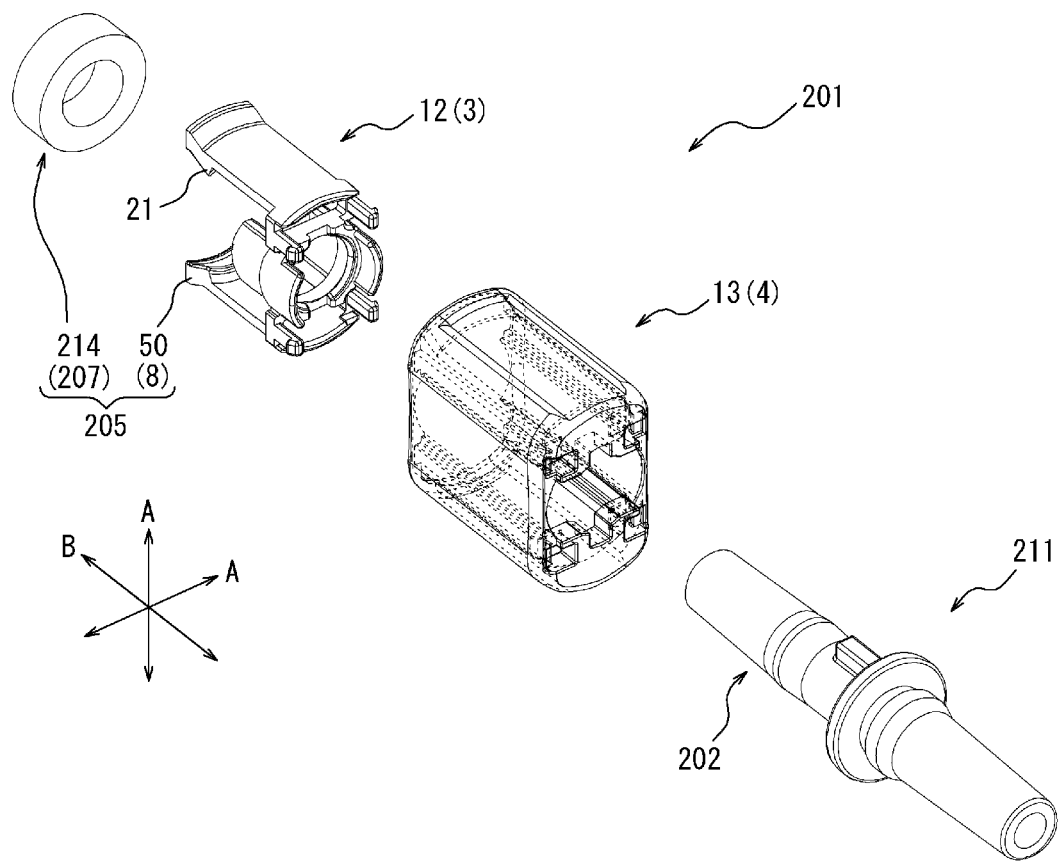
FIG. 7 is an exploded perspective view of the medical connector illustrated in FIG. 6 as seen from an angle different from that of FIG. 6.
Figure 8A:
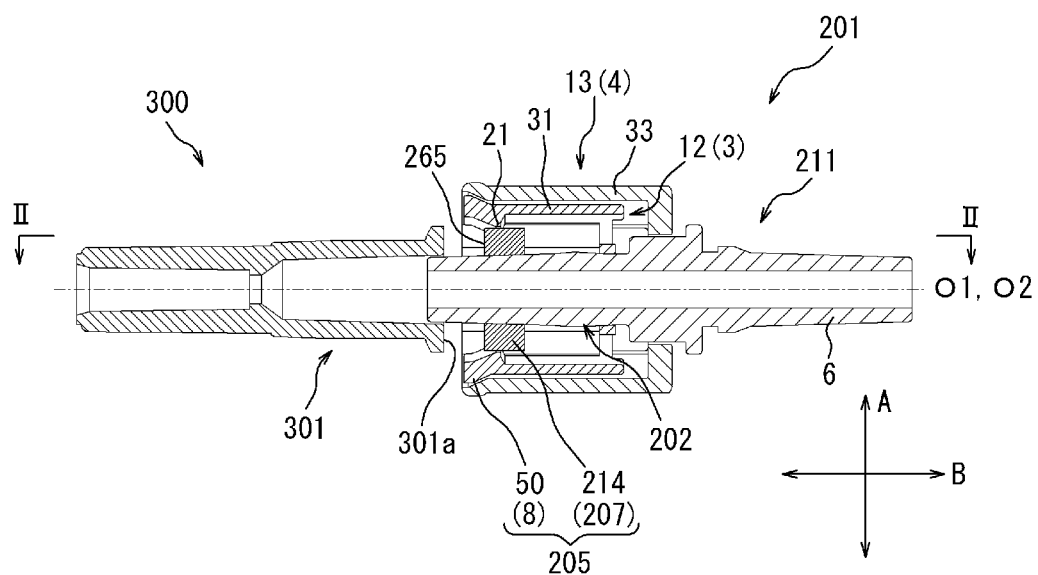
FIG. 8A is a longitudinal sectional view illustrating a separated state of the medical connector illustrated in FIG. 6 and a different medical connector connectable to the medical connector.
Figure 8B:
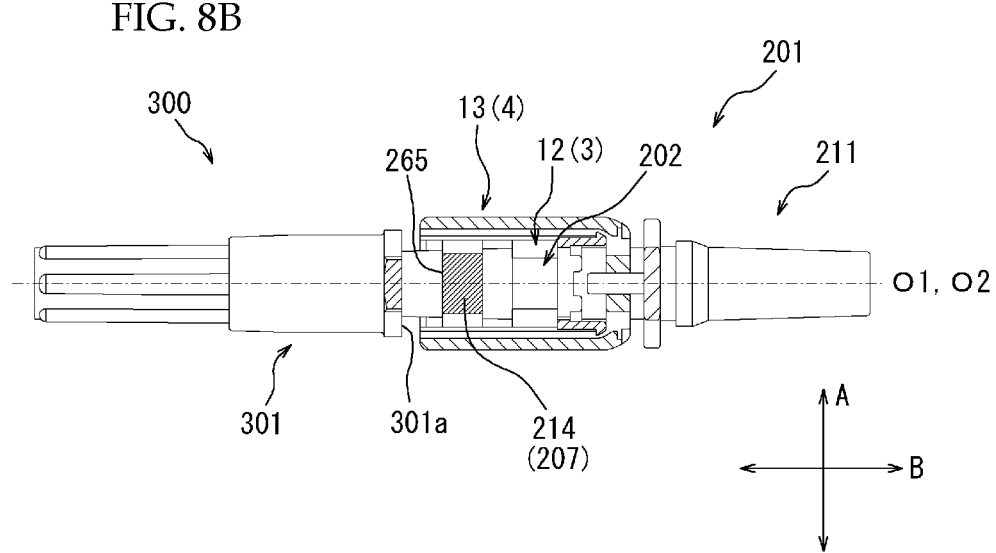
FIG. 8B is a cross-sectional view in the same separated state as in FIG. 8A.
Figure 9A:
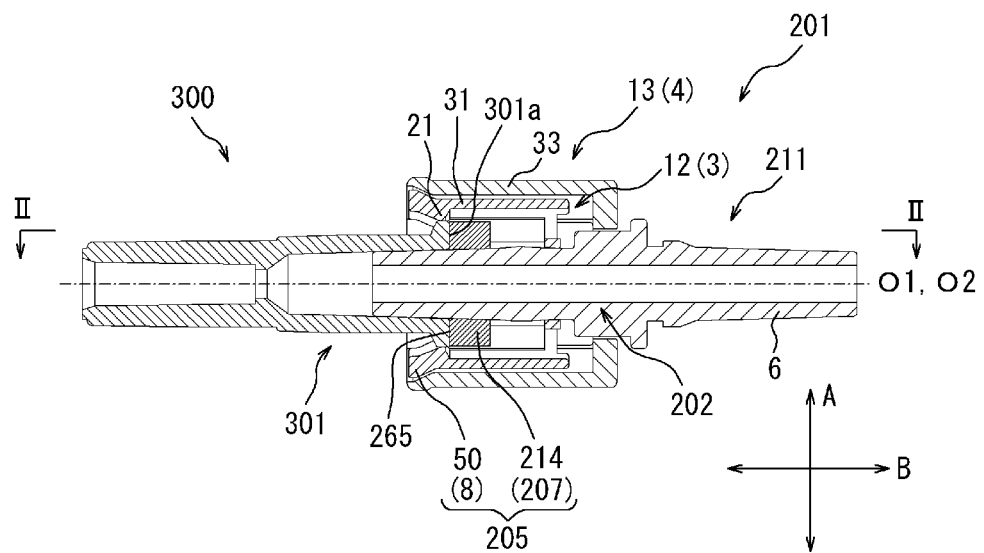
FIG. 9A is a longitudinal sectional view illustrating the medical connector illustrated in FIG. 8A and the different medical connector halfway connected.
Figure 9B:
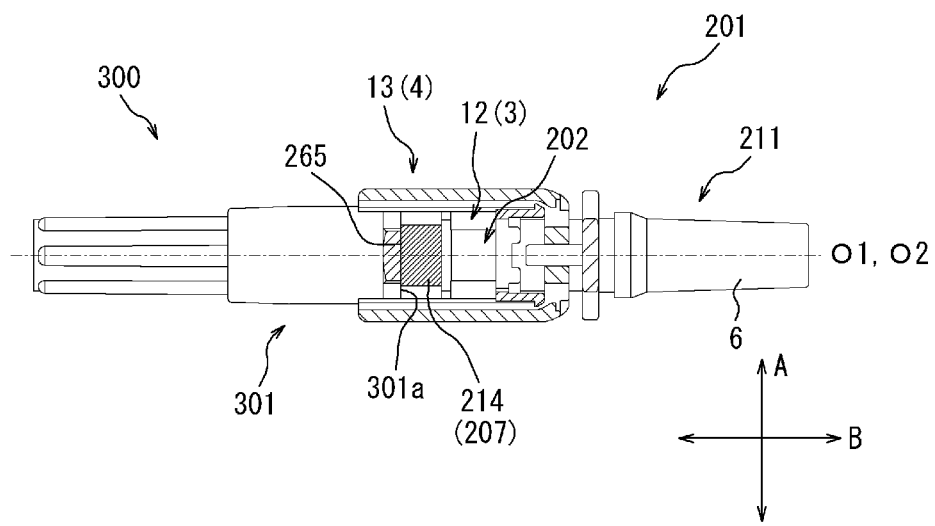
FIG. 9B is a cross-sectional view in the same halfway connected state in FIG. 9A.
Figure 10A:
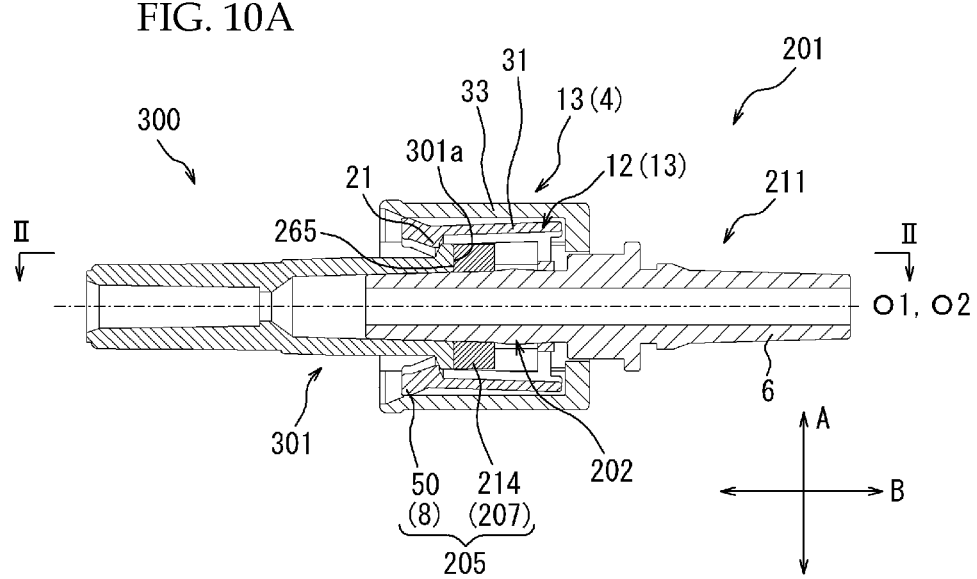
FIG. 10A is a longitudinal sectional view illustrating a state in which the medical connector illustrated in FIG. 8A is completely connected to the different medical connector.
Figure 10B:
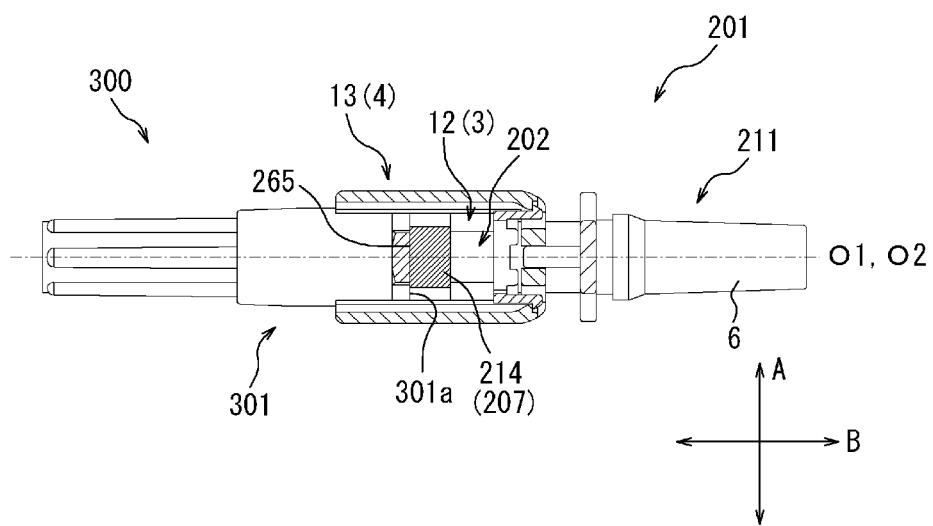
FIG. 10B is a cross-sectional view in the same completely connected state as in FIG. 10A.

FIG. 6 is an exploded perspective view of the medical connector 201, and FIG. 7 is an exploded perspective view as seen from an angle different from that of FIG. 6. FIG. 8A is a longitudinal sectional view illustrating a separated state before connection of the medical connector 201 and a different medical connector 300 connectable to the medical connector 201, and FIG. 8B is a cross-sectional view in the same separated state as in FIG. 8A. FIG. 9A is a longitudinal sectional view illustrating the medical connector 201 and the different medical connector 300 halfway connected, and FIG. 9B is a cross-sectional view in the same halfway connected state in FIG. 9A. FIG. 10A is a longitudinal sectional view illustrating a state in which the medical connector 201 is completely connected to the different medical connector 300, and FIG. 10B is a cross-sectional view in the same completely connected state as in FIG. 10A. FIGS. 8A, 9A, and 10A are longitudinal sectional views including a center axis O1 of a male connector unit 202 of the medical connector 201. FIGS. 8B, 9B, and 10B are cross-sectional views taken along line II-II in FIGS. 8A, 9A, and 10A, respectively.

The medical connector 201 illustrated in FIGS. 6 to 10 is different from the above-described medical connector 1 mainly in a configuration of an annular member and a configuration of an outer surface of the male connector unit on which the annular member is mounted; however, the configuration other than them is the same. Therefore, herein, the difference between the medical connector 201 and the above-described medical connector 1 is mainly described, and the description of common members and parts is not repeated.

As illustrated in FIGS. 6 and 7, an annular member 214 forming a spacer unit 207 of a blocking mechanism 205 of the medical connector 201 is formed of a simple tubular body made of a synthetic resin. As illustrated in FIGS. 8 to 10, the annular member 214 fits the male connector unit 202 such that an inner surface thereof is supported on the outer surface of the male connector unit 202 formed on a housing 211.

The housing 211 illustrated in FIG. 6 to FIG. 10 does not have a small diameter portion 62 (refer to FIG. 1 and the like) of the male connector unit 2 of a housing 11 of the above-described medical connector 1; however, the configuration other than this is similar to that of the housing 11 of the medical connector 1 described above. An outer peripheral surface of a distal end of the male connector unit 202 is formed into a tapered shape of which diameter gradually decreases in an axial direction B from a proximal side toward a distal side, and the annular member 214 fits a portion on which the tapered outer peripheral surface is formed of the male connector unit 202 as illustrated in FIG. 8A.

Connection operation between the medical connector 201 and the different medical connector 300 will next be described. The different medical connector 300 illustrated in FIGS. 8 to 10 is different from the above-described different medical connector 100 in that this does not include a first tapered portion 102a of the above-described different medical connector 100, but the configuration other than this is similar.

First, from the state in which the medical connector 201 and the different medical connector 300 are separated from each other as illustrated in FIG. 8, when the different medical connector 300 is held by a left hand and the locking member 13 of the medical connector 201 is held by a right hand, for example, the locking member 13 is moved in a direction to approach the different medical connector 300, and the male connector unit 202 of the medical connector 201 is inserted in a female connector unit 301 of the different medical connector 300, a top surface 301a of the female connector unit 301 abuts a distal end face 265 of the annular member 214 in an entire area in a circumferential direction of the male connector unit 202 as illustrated in FIG. 9. As a result, it becomes possible to liquid-tightly communicate a flow path in the male connector unit 202 and a flow path in the female connector unit 301.

When the locking member 13 is further moved from the state illustrated in FIG. 9 in a direction to approach the different medical connector 300, the annular member 214 is pressed by the top surface 301a of the female connector unit 301, and as a result, the annular member 214 slides on the outer surface of the male connector unit 202 from the distal side toward the proximal side in the axial direction B. As a result, as illustrated in FIG. 10, the tubular body as the annular member 214 moves from a position interposed between the clip 21 and the outer wall of the male connector unit 202 in the radial direction A. That is, in the state illustrated in FIG. 10, the blocking mechanism 205 changes from the blocked state illustrated in FIG. 9 to the movable state. In this manner, the blocking mechanism 205 of the medical connector 201 illustrated in FIGS. 6 to 10 moves the annular member 214 in the axial direction B of the male connector unit 202 without deforming the annular member 214 in the axial direction B of the male connector unit 202, so that it is possible to switch between the blocked state and the movable state. In other words, the annular member 214 forms the spacer unit 207 as a whole.

FIG. 10 illustrates a state in which the locking member 13 completely moves from the first position to the second position after the blocking mechanism 205 changes from the blocked state to the movable state.

Because the outer peripheral surface of the distal end of the male connector unit 202 has a tapered shape of which diameter gradually increases from the distal side toward the proximal side in the axial direction B, the inner peripheral surface of the annular member 214 is put into a state forcibly fitted to be in closer contact with the outer peripheral surface of the male connector unit 202 when this enters the state illustrated in FIG. 10 from the state illustrated in FIG. 9.

When separating the medical connectors from each other, by moving the locking member 13 from the second position to the first position, a plurality of plate pieces 31 of the engaging member 12 is restored from elastic deformation, and a plurality of clips 21 is retreated to an outer side in the radial direction A so as to move away from the female connector unit 301. Specifically, a plurality of clips 21 is moved to a state illustrated in FIG. 8 A. As a result, the locked state by the locking member 13 may be released. Then, after the locked state is released in this manner, at least one medical connector is moved in a direction away from the different medical connector in the axial direction B. As a result, the male connector unit 202 may be removed from the female connector unit 301.

As described above, because the annular member 214 illustrated in FIG. 10 is forcibly fitted onto the outer peripheral surface of the male connector unit 202, even if the male connector unit 202 is removed from the female connector unit 301, this is not restored to an initial position illustrated in FIG. 8. That is, unlike the medical connector 1 described above, the medical connector 201 illustrated in FIGS. 6 to 10 is configured to be switchable only once from the blocked state to the movable state.

The distal end face 265 of the annular member 214 illustrated in FIGS. 6 to 10 is formed of a plane orthogonal to the axial direction B; however, as the distal end face 65 of the annular member 14 of the above-described medical connector 1, this may also have a diameter reducing portion.

Second Embodiment

Next, a medical connector 401 of an embodiment different from the above-described medical connector 1 is described with reference to FIGS. 11 to 13.

Figure 11:
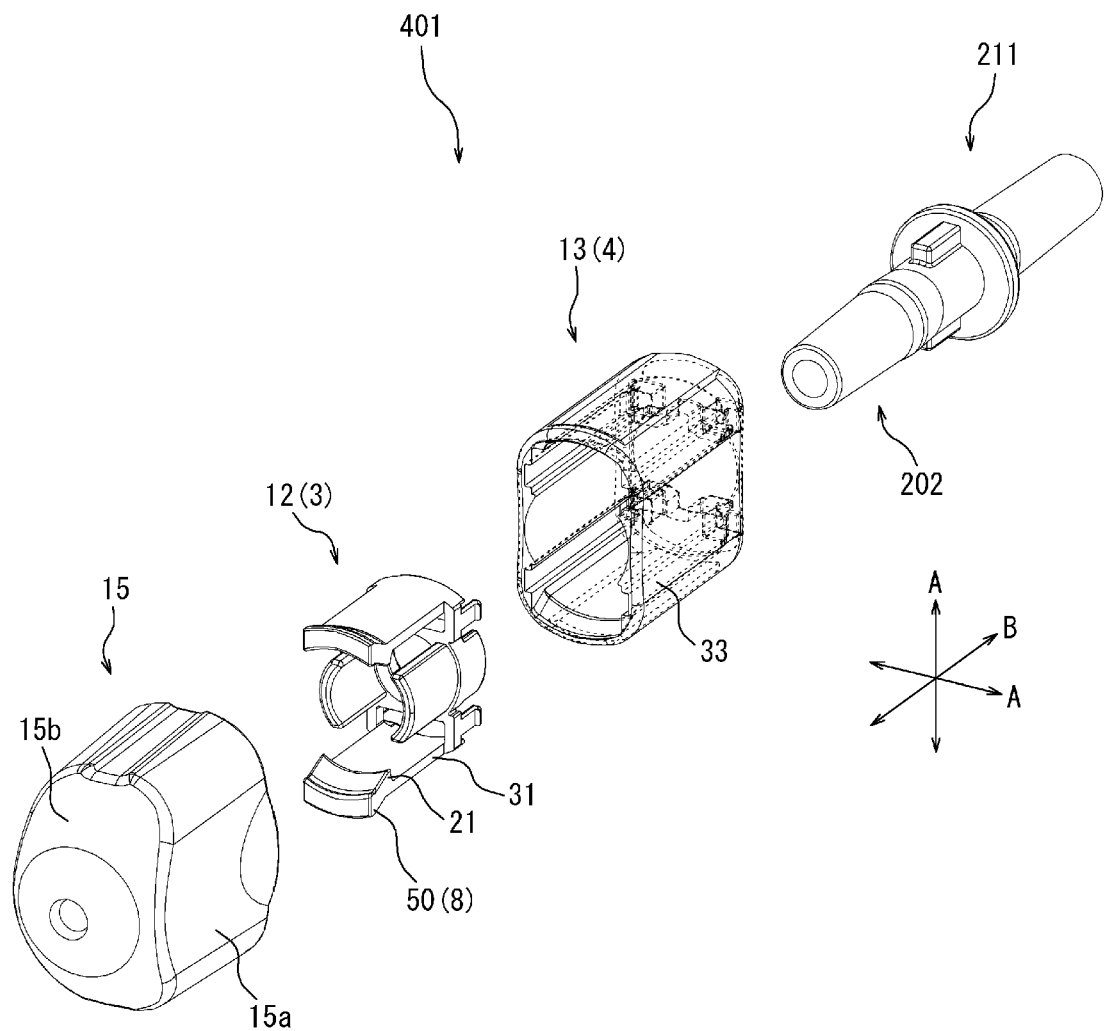
FIG. 11 is an exploded perspective view of a medical connector.
Figure 12:
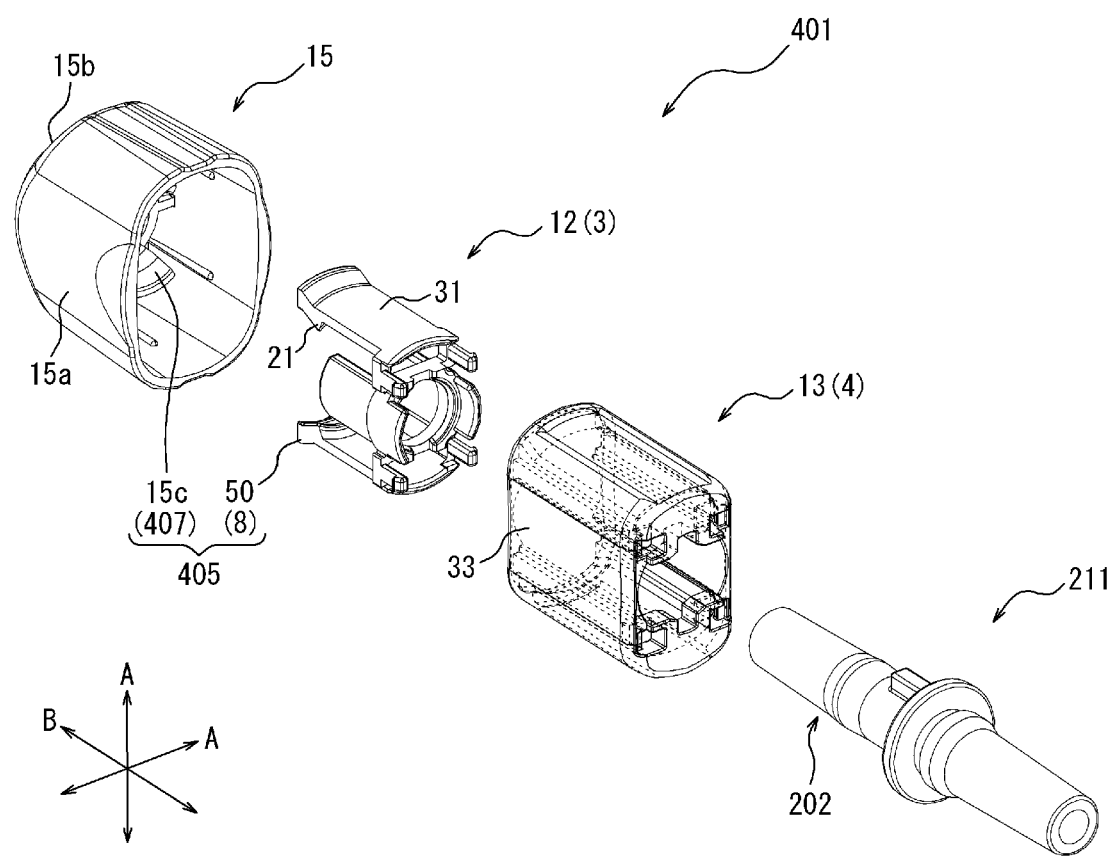
FIG. 12 is an exploded perspective view of the medical connector illustrated in FIG. 11 as seen from an angle different from that of FIG. 11.

FIG. 11 is an exploded perspective view of the medical connector 401 of this embodiment, and FIG. 12 is an exploded perspective view as seen from an angle different from that of FIG. 11. FIG. 13 is a longitudinal sectional view of the medical connector 401. FIG. 13 is a longitudinal sectional view including a center axis O1 of a male connector unit 202 of the medical connector 401.

As illustrated in FIG. 11, the medical connector 401 includes the male connector unit 202, an engaging unit 3, a locking unit 4, and a blocking mechanism 405.

The male connector unit 202 has the same configuration as that of a medical connector 201 illustrated in FIGS. 6 to 10, and this is similar to a male connector unit 2 of a medical connector 1 illustrated in FIGS. 1 to 5 except for a configuration of a small diameter portion 62. In other words, a housing 211 on which the male connector unit 202 is formed also has the same configuration as that of the medical connector 201 illustrated in FIGS. 6 to 10. Therefore, the detailed description thereof is not herein repeated. Because the engaging unit 3 and the locking unit 4 are similar to those of the medical connector 1 illustrated in FIGS. 1 to 5, the description thereof is not herein repeated.

The blocking mechanism 405 includes a spacer unit 407 which is interposed between the male connector unit 202 and a clip 21 in a blocked state and which is capable of holding a distance between the male connector unit 202 and the clip 21 to be a predetermined distance or longer and a stopper unit 8 of the engaging unit 3. Then, the blocking mechanism 405 of this embodiment may be switched from the blocked state to a movable state by moving the spacer unit 407 to a position in which it is allowed that the distance between the male connector unit 202 and the clip 21 becomes shorter than a predetermined distance (for example, a thickness in a radial direction A of the spacer unit 407).

More specifically, the medical connector 401 of this embodiment includes the housing 211 on which the male connector unit 202 is formed, an engaging member 12 fixed to the housing 211 and forming the engaging unit 3, a locking member 13 forming the locking unit 4 attached to the housing 211 so as to be slidable in an axial direction B of the male connector unit 202, and a cap member 15 on which the spacer unit 407 of the blocking mechanism 405 is formed.

Figure 13:
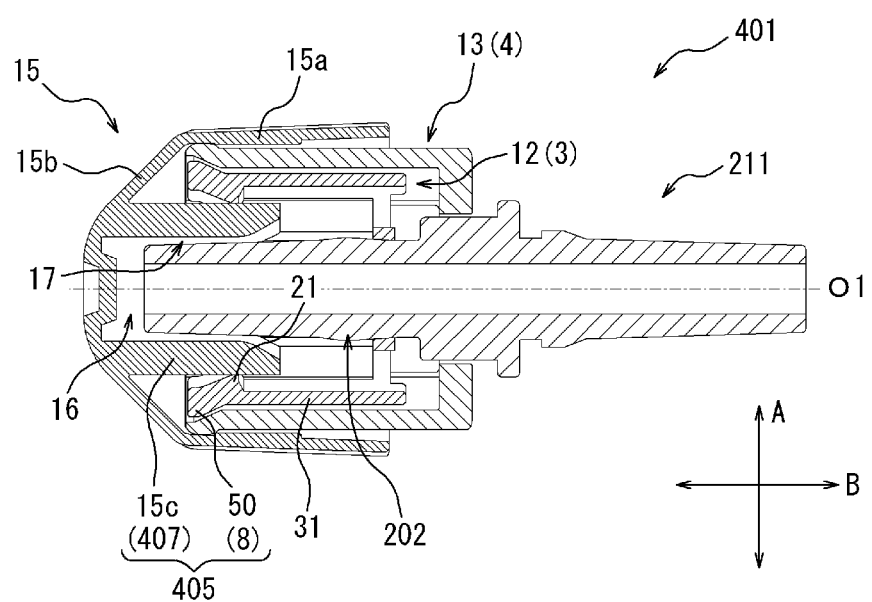
FIG. 13 is a longitudinal sectional view of the medical connector illustrated in FIG. 11.

The cap member 15 is detachably mounted so as to cover a distal end of the male connector unit 202, and as illustrated in FIGS. 11 to 13, this includes a tubular outer peripheral wall portion 15a, a top wall portion 15b which closes one end of the outer peripheral wall portion 15a, and a plurality of (two in this embodiment) projections 15c projecting from the top wall portion 15b inside the outer peripheral wall portion 15a.

As illustrated in FIG. 13, the cap member 15 is mounted such that an outer peripheral wall portion 15a covers a periphery of the locking member 13 in the radial direction A, and a top wall portion 15b covers the male connector unit 202, the engaging member 12, and the locking member 13 from a distal side in the axial direction B of the male connector unit 202. In this embodiment, by fitting the cap member 15 to the locking member 13 such that an inner surface of the outer peripheral wall portion 15a abuts an outer surface of a tubular wall 33 of the locking member 13, the cap member 15 is mounted on the locking member 13.

As illustrated in FIG. 13, a projection 15c of the cap member 15 is interposed between the outer surface of the male connector unit 202 and the clip 21 in a state in which the cap member 15 is mounted on the locking member 13. Therefore, in a mounted state of the cap member 15 illustrated in FIG. 13, a distance between the male connector unit 202 and the clip 21 is held to be a predetermined distance or larger due to presence of the projection 15c. In other words, the spacer unit 407 in the blocking mechanism 405 of this embodiment is formed of the projection 15c of the cap member 15.

By forming the spacer unit 407 on the cap member 15 in this manner, by mounting the cap member 15, a distal end of the male connector unit 202 may be protected from bacteria in the air and bacteria attached by contact of people or articles, and it is possible to prevent a user such as a doctor and a nurse from improperly moving the locking member 13 from the first position to the second position before use.

Then, by removing the cap member 15 from the locking member 13, the blocking mechanism 405 of this embodiment may be switched from the blocked state to the movable state. Specifically, by removing the cap member 15 from the locking member 13, the projection 15c as the spacer unit 407 may be moved from the position between the male connector unit 202 and the clip 21. As a result, the clip 21 may move inward in the radial direction A such that the distance between the male connector unit 202 and the clip 21 becomes shorter than a predetermined distance (for example, the thickness in the radial direction A of the spacer unit 407).

In such movable state of the blocking mechanism 405, the locking member 13 forming the locking unit 4 is moved from a proximal side toward the distal side in the axial direction B so as to slide with an outer peripheral side projection 50 as the stopper unit 8. By this movement, it is possible to press a plate piece 31 of the engaging member 12 forming the engaging unit 3 inward in the radial direction A via the stopper unit 8. Then, due to elastic deformation of the plate piece 31, it is possible to move the clip 21 inward in the radial direction A. In other words, the locking member 13 forming the locking unit 4 may be moved from the first position to the second position in the movable state of the blocking mechanism 405.

In this embodiment, the projections 15c as many as the clips 21 (two in this embodiment) are formed so as to be interposed between the outer surface of the male connector unit 202 and the respective clips 21. The projection 15c of this embodiment has a plate-like shape, but it is sufficient that this has a shape interposed between the male connector unit 202 and the clip 21 when the cap member 15 is mounted, and the shape is not limited to that in this embodiment.

Furthermore, the top wall portion 15b of this embodiment does not close a distal end opening of the male connector unit 202 in the state in which the cap member 15 is mounted on the locking member 13 (refer to FIG. 13), and a gap 16 is formed between the top wall portion 15b and a distal end face of the male connector unit 202. The projection 15c of this embodiment is interposed between the male connector unit 202 and the clip 21 in the state in which the cap member 15 is mounted on the locking member 13 (refer to FIG. 13) but a ventilation path 17 which allows ventilation to the outside of the medical connector 401 is formed between the male connector unit 202 and the projection 15c. Therefore, ventilation to the outside of the medical connector 401 of the distal end opening of the male connector unit 202 is allowed via the gap 16 and the ventilation path 17 in the state in which the cap member 15 is mounted on the locking member 13 (refer to FIG. 13). By providing such gap 16 and ventilation path 17, in an infusion set 500 (refer to FIG. 14) forming an infusion line provided with the medical connector 401 of this embodiment on a distal end as described later, it is possible to perform a priming process of filling the infusion line before use with liquid such as drug solution.

The cap member 15 of this embodiment is configured to be mounted on the locking member 13, but the configuration is not limited to this; for example, this may fit to the male connector unit 202 so as to abut the outer surface of the male connector unit 202 to be mounted on the male connector unit 202. However, in order to enable the above-described priming process, the ventilation to the outside of the medical connector 401 of the distal end opening of the male connector unit 202 is allowed. For example, it is possible that the distal end opening of the male connector unit 202 is not blocked and that a long groove which serves as a ventilation path is formed in the axial direction B in a portion that fits the male connector unit 202.

Finally, the infusion set 500 including the above-described medical connector 401 is described with reference to FIG. 14. The infusion set 500 illustrated in FIG. 14 includes the above-described medical connector 401, but this may be the infusion set provided with the medical connector 1 illustrated in FIGS. 1 to 5 and the medical connector 201 illustrated in FIGS. 6 to 10 in place of the medical connector 401. Herein, for convenience of description, the infusion set 500 including the medical connector 401 is described byway of example.

Figure 14:
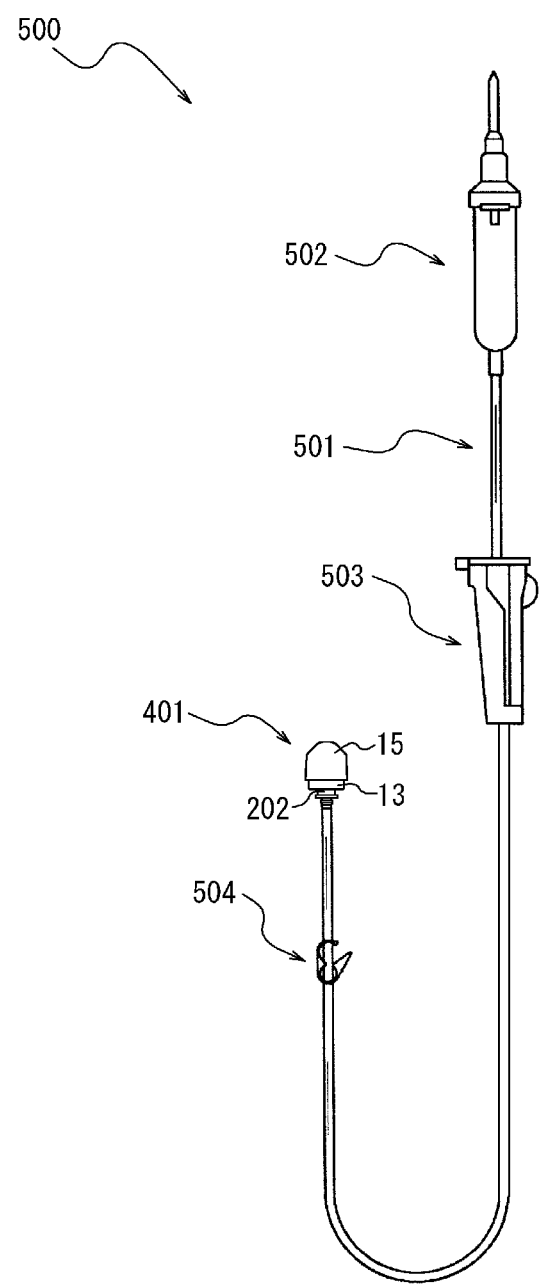
FIG. 14 is a view illustrating an infusion set provided with the medical connector illustrated in FIG. 11.

As illustrated in FIG. 14, the infusion set 500 forms the infusion line for connecting from an infusion holder such as an infusion bag not illustrated in FIG. 14 to an indwelling needle not illustrated in FIG. 14. Specifically, the infusion set 500 includes a plurality of medical tubes 501, a drip tube 502 capable of visually checking a flow rate of infusion solution supplied from the infusion holder, an adjusting clamp 503 capable of changing a flow rate of the infusion solution in the medical tube 501 to a plurality of states, a closing clamp 504 that closes the medical tube 501, and the medical connector 401 provided on a distal end of the medical tube 501 that is the distal end of the infusion line.

It is sufficient that the infusion set 500 includes at least the medical tube 501 and the medical connector 401, and this may also be the infusion set in which no other member is present or to which a different member is added.

According to the infusion set 500 illustrated in FIG. 14, for example, by connecting a proximal end which is an upstream end of the infusion line to the infusion holder and connecting the distal end which is a downstream end to an indwelling needle hub and the indwelling needle, the infusion to the patient may be performed. However, it is necessary to perform the above-described priming process before administration to the patient by the infusion line. Because the cap member 15 of the medical connector 401 does not close the distal end opening of the male connector unit 202, it is possible to perform the priming process while the cap member 15 is mounted.

The medical connector according to the present invention is not limited to the specific configuration described in the above embodiment and may be variously configured without departing from the scope of claims. For example, in the blocking mechanism 5 of the above-described medical connector 1 (refer to FIG. 1 and the like), the position of the following portion 64 and the position of the clip 21 overlap each other in the axial direction B in the blocked state (refer to FIG. 3 and the like), but it is only necessary to limit the amount of movement of the clip 21 inward in the radial direction A to be less than a predetermined amount, and the positions of the following portion 64 and the clip 21 in the axial direction B are not necessarily the same. Therefore, the blocking mechanism may be put into the blocked state in a state in which the positions of the following portion 64 and the clip 21 in the axial direction B are different from each other. This also applies to the above-described medical connector 201 (refer to FIGS. 6 to 10).

INDUSTRIAL APPLICABILITY

The present disclosure relates to a medical connector and a connecting method of a medical connector.

REFERENCE NUMERAL LIST

1 Medical connector
2 Male connector unit
3 Engaging unit
4 Locking Unit
5 Blocking mechanism
6 Connecting unit
7 Spacer unit
8 Stopper unit
11 Housing
12 Engaging member
13 Locking member
14 Annular member
15 Cap member
15a Outer peripheral wall portion
15b Top wall portion
15c Projection
16 Gap
17 Ventilation path
21 Clip
21a Tapered surface on distal side
21b Tapered surface on proximal side
31 Plate piece
33 Tubular wall
33a Rotation blocking unit
34 Bottom wall
35 Through hole
36 Opening
37 Concave portion
38 Rib
39 Tapered surface
40 Bottom wall
41 Through hole 42 Projection
43 Engaging member side clip
44 Guide piece
46 Locking member side clip
47 Flange
50 Outer peripheral side projection
50a Tapered surface
60 Distal side stepped surface
61 Proximal side stepped surface
62 Small diameter portion
63 Deformable portion
64 Following portion
65 Distal end face
65a Diameter reducing portion
100 Different medical connector
101 Female connector unit
101a Top surface
101b Peripheral wall portion
101b1 Engaging convex portion
102a First tapered portion
102b Second tapered portion
201 Medical connector
202 Male connector unit
205 Blocking mechanism
207 Spacer unit
214 Annular member
265 Distal end face
300 Different medical connector
301 Female connector unit
301a Top surface
401 Medical connector
405 Blocking mechanism
407 Spacer unit
500 Infusion set
501 Medical tube
502 Drip tube
503 Adjusting clamp
504 Blocking clamp
14' Annular member
63' Deformable portion
64' Following portion
65' Distal end face
65a' Diameter reducing portion
65b' Annular flat surface portion
A Radial direction of male connector unit
B Axial direction of male connector unit
O1 Center axis of male connector unit
O2 Center axis of female connector unit

What is claimed is:

1. A medical connector comprising:
a tubular male connector unit;
an engaging unit located on an outer side of the male connector unit in a radial direction of the male connector unit, wherein at least a part of the engaging unit is elastically deformable inward in the radial direction;
a locking unit movable between a first position and a second position in which at least the part of the engaging unit is elastically deformed inward in the radial direction relative to the first position; and
a blocking mechanism comprising a spacer unit interposed between the male connector unit and the engaging unit in the radial direction, the blocking mechanism configured to block the locking unit from moving from the first position to the second position in a predetermined state.

2. The medical connector according to claim 1,
wherein the blocking mechanism is changeable between a blocked state in which the locking unit is blocked from moving from the first position to the second position and a movable state in which the locking unit is movable from the first position to the second position.

3. The medical connector according to claim 2,
wherein the engaging unit comprises:
a clip that is engageable with a female connector unit of a different medical connector by moving inward in the radial direction, and
a stopper unit formed on a wall surface on an outer side in the radial direction;
wherein the locking unit abuts the stopper unit in the blocked state;
wherein the blocking mechanism further comprises the stopper unit of the engaging unit; and
wherein the spacer unit is interposed between the male connector unit and the clip in the blocked state, the spacer unit being configured to maintain a distance between the male connector unit and the clip to be a predetermined distance or longer.

4. The medical connector according to claim 3,
wherein the blocking mechanism is configured to switch from the blocked state to the movable state by moving or deforming the spacer unit to a position in which a distance between the male connector unit and the clip is shorter than the predetermined distance; and
wherein, when the blocking mechanism is in the movable state, the locking unit is configured to slide with the stopper unit to press the engaging unit inward in the radial direction, thereby moving the clip inward in the radial direction, and to move from the first position to the second position.

5. The medical connector according to claim 4,
wherein the spacer unit is configured to be pressed by the female connector unit to move or deform when the male connector unit is inserted in the female connector unit of the different medical connector so that the blocking mechanism is switched from the blocked state to the movable state.

6. The medical connector according to claim 5,
wherein the locking unit is configured to move from the first position to the second position in conjunction with the blocking mechanism switching from the blocked state to the movable state when the male connector unit is inserted in the female connector unit.

7. The medical connector according to claim 5,
wherein the spacer unit is formed on an annular member located between the male connector unit and the engaging unit.

8. The medical connector according to claim 7,
wherein the blocking mechanism is configured to switch between the blocked state and the movable state by moving the annular member in an axial direction of the male connector unit.

9. The medical connector according to claim 7,
wherein the annular member comprises:
a deformable portion that is deformable in an axial direction of the male connector unit, and
a following portion that is movable in the axial direction following the deformation of the deformable portion; and wherein the blocking mechanism is configured to switch between:
- the blocked state, in which the following portion is located between the male connector unit and the clip, and
- the movable state, in which the following portion is not located between the male connector unit and the clip, due to deformation of the deformable portion.

10. The medical connector according to claim 9,
wherein the following portion comprises a distal end face having a diameter reducing portion with a diameter that gradually decreases toward a distal side of the male connector unit on a distal side portion of the male connector unit, and
the diameter reducing portion is configured to be brought into contact with the female connector unit in a circumferential area of the diameter reducing portion when the male connector unit is inserted in the female connector unit.

11. The medical connector according to claim 7,
wherein the annular member comprises:
- a deformable portion that is deformable in an axial direction of the male connector unit, and
- a following portion that is deformable in the axial direction following the deformation of the deformable portion; and wherein the blocking mechanism is configured to switch between:
- the blocked state, in which the following portion is located between the male connector unit and the clip and is in a state with a predetermined thickness or larger in the radial direction by the deformation of the deformable portion, and
- the movable state, in which the following portion is located between the male connector unit and the clip and is in a state with less than the predetermined thickness in the radial direction by the deformation of the deformable portion.

12. The medical connector according to claim 3,
wherein the spacer unit is formed on a cap member that is detachably mounted so as to cover a distal end of the male connector unit.

13. A method of connecting a medical connector to a different medical connector, the method comprising:
providing the medical connector, which comprises:
- a tubular male connector unit,
- an engaging unit located on an outer side of the male connector unit in a radial direction of the male connector unit, wherein at least a part of the engaging unit is elastically deformable inward in the radial direction,
- a locking unit that is movable between a first position and a second position in which at least the part of the engaging unit is elastically deformed inward in the radial direction relative to the first position, and
- a spacer unit interposed between the male connector unit and the engaging unit;

providing the different medical connector, which comprises a female connector unit in which the male connector unit is insertable;
inserting the male connector unit of the medical connector in the female connector unit of the different medical connector;
changing from a blocked state in which the locking unit is blocked from moving from the first position to the second position to a movable state in which the locking unit is movable from the first position to the second position by movement or deformation of the spacer unit when the spacer unit is pressed by the female connector unit; and
engaging the engaging unit with the female connector unit by elastic deformation inward in the radial direction when the locking unit moves from the first position to the second position and presses the engaging unit inward in the radial direction.

14. A method of connecting a medical connector to a different medical connector, the method comprising:
providing the medical connector, which comprises:
- a tubular male connector unit,
- an engaging unit located on an outer side of the male connector unit in a radial direction of the male connector unit, wherein at least a part of the engaging unit is elastically deformable inward in the radial direction,
- a locking unit that is movable between a first position and a second position in which at least the part of the engaging unit is elastically deformed inward in the radial direction relative to the first position, and
- a blocking mechanism comprising a spacer unit interposed between the male connector unit and the engaging unit in the radial direction, the blocking mechanism configured to block the locking unit from moving from the first position to the second position in a blocked state;

providing the different medical connector, which comprises a female connector unit in which the male connector unit is insertable;
inserting the male connector unit of the medical connector in the female connector unit of the different medical connector;
changing from the blocked state in which the locking unit is blocked from moving from the first position to the second position to a movable state in which the locking unit is movable from the first position to the second position; and
engaging the engaging unit with the female connector unit by elastic deformation inward in the radial direction when the locking unit moves from the first position to the second position and presses the engaging unit inward in the radial direction.

* * * * *

UNITED STATES PATENT AND TRADEMARK OFFICE
CERTIFICATE OF CORRECTION

Page 1 of 1

PATENT NO. : 11,160,967 B2
APPLICATION NO. : 16/225225
DATED : November 2, 2021
INVENTOR(S) : Fujieda et al.

It is certified that error appears in the above-identified patent and that said Letters Patent is hereby corrected as shown below:

On the Title Page

Item (73) Assignee:
Please delete:
"TERUMO KABUSHTKT KAISHA"
Please replace with:
TERUMO KABUSHIKI KAISHA Signed and Sealed this
Twenty-ninth Day of March, 2022

Drew Hirshfeld
*Performing the Functions and Duties of the
Under Secretary of Commerce for Intellectual Property and
Director of the United States Patent and Trademark Office*